US012589229B2

(12) United States Patent
Sonkusale et al.

(10) Patent No.: US 12,589,229 B2
(45) Date of Patent: Mar. 31, 2026

(54) MACROPOROUS SOLID HARD MICRONEEDLES WITH EMBEDDED PARTICULATE DRUGS

(71) Applicant: Trustees of Tufts College, Medford, MA (US)

(72) Inventors: Sameer Sonkusale, Medford, MA (US); Aydin Sadeqi, Medford, MA (US); Hojatollah Rezaei Nejad, Boston, MA (US); Jake Lombardo, Boston, MA (US); Konstantinos Tzortzakis, Boston, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 18/507,889

(22) Filed: Nov. 13, 2023

(65) Prior Publication Data

US 2024/0075268 A1 Mar. 7, 2024

Related U.S. Application Data

(63) Continuation of application No. PCT/US2022/029078, filed on May 12, 2022.

(60) Provisional application No. 63/212,586, filed on Jun. 18, 2021, provisional application No. 63/201,812, filed on May 13, 2021.

(51) Int. Cl.
A61M 37/00 (2006.01)

(52) U.S. Cl.
CPC . A61M 37/0015 (2013.01); A61M 2037/0023 (2013.01); A61M 2037/0046 (2013.01)

(58) Field of Classification Search
CPC ...... A61M 37/0015; A61M 2037/0023; A61M 2037/0046
See application file for complete search history.

(56) References Cited

U.S. PATENT DOCUMENTS

| | | | |
|---|---|---|---|
| 5,527,288 A | 6/1996 | Gross et al. | |
| 5,611,806 A | 3/1997 | Jang | |
| 7,344,499 B1 | 3/2008 | Prausnitz et al. | |
| 11,103,686 B2 | 8/2021 | Nejad et al. | |
| 2002/0082543 A1* | 6/2002 | Park .................. | A61M 37/0015 |
| | | | 604/20 |

(Continued)

FOREIGN PATENT DOCUMENTS

| | | | | |
|---|---|---|---|---|
| GB | 2506010 A | 3/2014 | | |
| KR | 20150085502 A | * 7/2015 | ........ | A61M 37/0015 |

(Continued)

OTHER PUBLICATIONS

Totally Seals website screen shot, from the wayback machine publication date of at least as early as Aug. 14, 2020, available at https://web.archive.org/web/20200814191113/https://www.totallyseals.com/blogs/news/what-is-shore-hardness Jan. 9, 2024. (Year: 2020).*

(Continued)

*Primary Examiner* — Dung T Ulsh
*Assistant Examiner* — Fatimata Sahra Diop
(74) *Attorney, Agent, or Firm* — Quarles & Brady LLP

(57) ABSTRACT

The present disclosure provides microneedles and microneedle patches for transdermal drug delivery and methods of making and using the same. The microneedles are porous and contain a drug in particulate form within the pores.

24 Claims, 21 Drawing Sheets

(56) References Cited

U.S. PATENT DOCUMENTS

| | | | |
|---|---|---|---|
| 2005/0251088 A1 | 11/2005 | Kwon | |
| 2008/0312610 A1* | 12/2008 | Binks | A61P 31/10 |
| | | | 264/45.6 |
| 2009/0035446 A1 | 2/2009 | Kwon | |
| 2010/0312191 A1 | 12/2010 | Allen et al. | |
| 2011/0137254 A1 | 6/2011 | Scholten et al. | |
| 2011/0190688 A1* | 8/2011 | Tagliaferri | A61M 37/00 |
| | | | 604/20 |
| 2016/0129164 A1 | 5/2016 | Lee et al. | |
| 2017/0368322 A1* | 12/2017 | Kato | A61M 37/00 |
| 2018/0064920 A1 | 3/2018 | Desimone et al. | |
| 2018/0326195 A1* | 11/2018 | Yamabe | A61M 37/0015 |
| 2019/0046479 A1* | 2/2019 | Pathak | A61M 37/0076 |
| 2020/0155475 A1 | 5/2020 | Lakhani et al. | |
| 2022/0249819 A1* | 8/2022 | Faisal | A61K 9/0021 |

FOREIGN PATENT DOCUMENTS

| | | | |
|---|---|---|---|
| WO | 2003092785 A1 | 11/2003 | |
| WO | 2009113856 A1 | 9/2009 | |
| WO | 2018226563 A1 | 12/2018 | |
| WO | 2019203888 A2 | 10/2019 | |
| WO | 2021007344 A1 | 1/2021 | |

OTHER PUBLICATIONS

TotallySealswebsitescreenshot,fromthewaybackmachinepublication dateofatleastasearlyasAug. 14, 2020,availableathttps://web.archive. org/web/20200814191113/https:/Avww.totallyseals.com/blogs/news/ what-is-shore-hardness Jan. 9, 2024 (Year: 2020).*

Sánchez-Leija, R. J., et al. "Controlled release of lidocaine hydrochloride from polymerized drug-based deep-eutectic solvents." Journal of Materials Chemistry B 2.43 (2014): 7495-7501.

Schipper, Pim, et al. "Repeated fractional intradermal dosing of an inactivated polio vaccine by a single hollow microneedle leads to superior immune responses." Journal of Controlled Release 242 (2016): 141-147.

Shirkhanzadeh, M. "Microneedles coated with porous calcium phosphate ceramics: effective vehicles for transdermal delivery of solid trehalose." Journal of Materials Science: Materials in Medicine 16 (2005): 37-45.

Smith, Eric Wane, and Howard I. Maibach. Percutaneous penetration enhancers. CRC Press, 1995.

Stoeber, Boris, and Dorian Liepmann. "Arrays of hollow out-of-plane microneedles for drug delivery." Journal of microelectromechanical systems 14.3 (2005): 472-479.

Sugiyama, Susumu, Sommawan Khumpuang, and Gaku Kawaguchi. "Plain-pattern to cross-section transfer (PCT) technique for deep x-ray lithography and applications." Journal of Micromechanics and Microengineering 14.10 (2004): 1399.

Sullivan, Sean P., et al. "Dissolving polymer microneedle patches for influenza vaccination." Nature medicine 16.8 (2010): 915-920.

Takahashi, Hidetoshi, et al. "Scalable fabrication of microneedle arrays via spatially controlled UV exposure." Microsystems & nanoengineering 2.1 (2016): 1-9.

Tang, Yemin, et al. "Ultra deep reactive ion etching of high aspect-ratio and thick silicon using a ramped-parameter process." Journal of Microelectromechanical Systems 27.4 (2018): 686-697.

Trautmann, Anika, et al. "Towards a versatile point-of-care system combining femtosecond laser generated microfluidic channels and direct laser written microneedle arrays." Microsystems & Nanoengineering 5.1 (2019): 6.

Van der Maaden, Koen, et al. "Microneedle-based drug and vaccine delivery via nanoporous microneedle arrays." Drug delivery and translational research 5 (2015): 397-406.

Verhoeven, Michel, et al. "Applying ceramic nanoporous microneedle arrays as a transport interface in egg plants and an ex-vivo human skin model." Microelectronic engineering 98 (2012): 659-662.

Vora, Lalit K., et al. "Novel bilayer dissolving microneedle arrays with concentrated PLGA nano-microparticles for targeted intradermal delivery: Proof of concept." Journal of Controlled Release 265 (2017): 93-101.

Vrdoljak, Anto, et al. "Coated microneedle arrays for transcutaneous delivery of live virus vaccines." Journal of controlled release 159.1 (2012): 34-42.

Wang, Ping M., et al. "Precise microinjection into skin using hollow microneedles." Journal of investigative dermatology 126.5 (2006): 1080-1087.

Wilke, Nicolle, et al. "Process optimization and characterization of silicon microneedles fabricated by wet etch technology." Microelectronics Journal 36.7 (2005): 650-656.

Xiang, Zhuolin, et al. "Dense vertical SU-8 microneedles drawn from a heated mold with precisely controlled volume." Journal of Micromechanics and Microengineering 25.2 (2015): 025013.

Xue, Peng, et al. "Flexible PEGDA-based microneedle patches with detachable PVP-CD arrowheads for transdermal drug delivery." RSC Advances 5.92 (2015): 75204-75209.

Gao, Ya, et al. "Transdermal delivery of therapeutics through dissolvable gelatin/sucrose films coated on PEGDA microneedle arrays with improved skin permeability." Journal of Materials Chemistry B 7.47 (2019): 7515-7524.

Yoon, Y-K., J-H. Park, and Mark G. Allen. "Multidirectional UV lithography for complex 3-D MEMS structures." Journal of microelectromechanical systems 15.5 (2006): 1121-1130.

Zhang, Ying, et al. "Development of lidocaine-coated microneedle product for rapid, safe, and prolonged local analgesic action." Pharmaceutical research 29 (2012): 170-177.

Amsden, B. G., and M. F. A. Goosen. "Transdermal delivery of peptide and protein drugs: an overview." AIChE journal 41.8 (1995): 1972-1997.

Bediz, Bekir, et al. "Dissolvable microneedle arrays for intradermal delivery of biologics: fabrication and application." Pharmaceutical research 31 (2014): 117-135.

Bystrova, S., and R. Luttge. "Micromolding for ceramic microneedle arrays." Microelectronic engineering 88.8 (2011): 1681-1684.

Cahill, Ellen M., et al. "Metallic microneedles with interconnected porosity: A scalable platform for biosensing and drug delivery." Acta Biomaterialia 80 (2018): 401-411.

Cai, Bing, et al. "Self-setting bioceramic microscopic protrusions for transdermal drug delivery." Journal of Materials Chemistry B 2.36 (2014): 5992-5998.

Choina, J., et al. "Photocatalytic decomposition of pharmaceutical ibuprofen pollutions in water over titania catalyst." Applied Catalysis B: Environmental 129 (2013): 589-598.

Davis, Shawn P., et al. "Insertion of microneedles into skin: measurement and prediction of insertion force and needle fracture force." Journal of biomechanics 37.8 (2004): 1155-1163.

Demir, Yusuf K., Zafer Akan, and Oya Kerimoglu. "Characterization of polymeric microneedle arrays for transdermal drug delivery." PloS one 8.10 (2013): e77289.

DeMuth, Peter C., et al. "Polymer multilayer tattooing for enhanced DNA vaccination." Nature materials 12.4 (2013): 367-376.

DeMuth, Peter C., et al. "Vaccine delivery with microneedle skin patches in nonhuman primates." Nature biotechnology 31.12 (2013): 1082-1085.

Friedman, Paul M., et al. "Topical anesthetics update: EMLA and beyond." Dermatologic surgery 27.12 (2001): 1019-1026.

Gardeniers, Han JGE, et al. "Silicon micromachined hollow microneedles for transdermal liquid transport." Journal of Microelectromechanical systems 12.6 (2003): 855-862.

Gill, Harvinder S., et al. "Cutaneous vaccination using microneedles coated with hepatitis C DNA vaccine." Gene therapy 17.6 (2010): 811-814.

Griss, Patrick, and Göran Stemme. "Side-opened out-of-plane microneedles for microfluidic transdermal liquid transfer." Journal of Microelectromechanical systems 12.3 (2003): 296-301.

Gupta, Jyoti, et al. "Rapid local anesthesia in human subjects using minimally invasive microneedles." The Clinical journal of pain 28.2 (2012): 129.

(56)　　　　　References Cited

OTHER PUBLICATIONS

Han, Manhee, et al. "A novel fabrication process for out-of-plane microneedle sheets of biocompatible polymer." Journal of Micromechanics and Microengineering 17.6 (2007): 1184.

Henry, Sebastien, et al. "Microfabricated microneedles: a novel approach to transdermal drug delivery." Journal of pharmaceutical sciences 87.8 (1998): 922-925.

Humrez, Laith, et al. "Synthesis and characterisation of porous polymer microneedles." Journal of Polymer Research 18 (2011): 1043-1052.

Ji, Jing, et al. "Microfabricated microneedle with porous tip for drug delivery." Journal of Micromechanics and Microengineering 16.5 (2006): 958.

Kamari, Younes, and Mehran Ghiaci. "Preparation and characterization of ibuprofen/modified chitosan/TiO2 hybrid composite as a controlled drug-delivery system." Microporous and Mesoporous Materials 234 (2016): 361-369.

Kaur, Monika, et al. "Microneedle-assisted delivery of verapamil hydrochloride and amlodipine besylate." European journal of pharmaceutics and biopharmaceutics 86.2 (2014): 284-291.

Kim, Jooncheol, et al. "Maskless fabrication of high aspect ratio structures by combination of micromolding and direct drawing." 2011 IEEE 24th International Conference on Micro Electro Mechanical Systems. IEEE, 2011.

Kim, Kabseog, et al. "A tapered hollow metallic microneedle array using backside exposure of SU-8." Journal of Micromechanics and Microengineering 14.4 (2004): 597.

Kochhar, Jaspreet Singh, et al. "Microneedle integrated transdermal patch for fast onset and sustained delivery of lidocaine." Molecular pharmaceutics 10.11 (2013): 4272-4280.

Krieger, Kevin J., et al. "Simple and customizable method for fabrication of high-aspect ratio microneedle molds using low-cost 3D printing." Microsystems & nanoengineering 5.1 (2019): 42.

Lagreca, Elena, et al. "Recent advances in the formulation of PLGA microparticles for controlled drug delivery." Progress in biomaterials 9 (2020): 153-174.

Lahiji, Shayan F., Manita Dangol, and Hyungil Jung. "A patchless dissolving microneedle delivery system enabling rapid and efficient transdermal drug delivery." Scientific reports 5.1 (2015): 7914.

Lee, Kwang, et al. "Drawing lithography: three-dimensional fabrication of an ultrahigh-aspect-ratio microneedle." Advanced Materials 22.4 (2010): 483-486.

Lee, Byeong-Min, et al. "Dissolving microneedles for rapid and painless local anesthesia." Pharmaceutics 12.4 (2020): 366.

Lee, Jeong W., Jung-Hwan Park, and Mark R. Prausnitz. "Dissolving microneedles for transdermal drug delivery." Biomaterials 29.13 (2008): 2113-2124.

Lee, Kwang, Chang Yoel Lee, and Hyungil Jung. "Dissolving microneedles for transdermal drug administration prepared by step-wise controlled drawing of maltose." Biomaterials 32.11 (2011): 3134-3140.

Lee, Yunwoo, et al. "Drug-delivery system based on salmon DNA nano-and micro-scale structures." Scientific reports 7.1 (2017): 9724.

Li, Yan, et al. "Fabrication of sharp silicon hollow microneedles by deep-reactive ion etching towards minimally invasive diagnostics." Microsystems & nanoengineering 5.1 (2019): 41.

Lim, Jungeun, et al. "Design rules for a tunable merged-tip microneedle." Microsystems & nanoengineering 4.1 (2018): 29.

Lin, Tsung-Hung, Ching-Kong Chao, and Shih-Yu Hung. "A novel fabrication method of micro-needle mold by using the micro-lens mask through contact printing." Microsystem Technologies 21 (2015): 1843-1848.

Manoukian, Martin Anthony Christopher, et al. "Topical administration of ibuprofen for injured athletes: considerations, formulations, and comparison to oral delivery." Sports medicine—open 3 (2017): 1-9.

Medhi, Pangkhi, et al. "Lidocaine-loaded fish scale-nanocellulose biopolymer composite microneedles." Aaps Pharmscitech 18 (2017): 1488-1494.

Migalska, Katarzyna, et al. "Laser-engineered dissolving microneedle arrays for transdermal macromolecular drug delivery." Pharmaceutical research 28 (2011): 1919-1930.

Miyano, Takaya, et al. "Sugar micro needles as transdermic drug delivery system." Biomedical Microdevices 7 (2005): 185-188.

Moon, Sang Jun, et al. "Fabrication of microneedle array using LIGA and hot embossing process." Microsystem technologies 11 (2005): 311-318.

Nejad, Hojatollah Rezaei, et al. "Low-cost and cleanroom-free fabrication of microneedles." Microsystems & nanoengineering 4.1 (2018): 1-7.

Omatsu, Takashige, et al. "Metal microneedle fabrication using twisted light with spin." Optics express 18.17 (2010): 17967-17973.

Park, Jung-Hwan, Mark G. Allen, and Mark R. Prausnitz. "Biodegradable polymer microneedles: fabrication, mechanics and transdermal drug delivery." Journal of controlled release 104.1 (2005): 51-66.

Park, Jung-Hwan, et al. "Polymer particle-based micromolding to fabricate novel microstructures." Biomedical microdevices 9 (2007): 223-234.

Park, Jung-Hwan, et al. "Tapered conical polymer microneedles fabricated using an integrated lens technique for transdermal drug delivery." IEEE transactions on biomedical engineering 54.5 (2007): 903-913.

Prausnitz, Mark R. "Microneedles for transdermal drug delivery." Advanced drug delivery reviews 56.5 (2004): 581-587.

Faraji Rad, Zahra, et al. "High-fidelity replication of thermoplastic microneedles with open microfluidic channels." Microsystems & nanoengineering 3.1 (2017): 1-11.

Rowbotham, Michael C., Pamela S. Davies, and Howard L. Fields. "Topical lidocaine gel relieves postherpetic neuralgia." Annals of Neurology: Official Journal of the American Neurological Association and the Child Neurology Society 37.2 (1995): 246-253.

Roxhed, Niclas, Patrick Griss, and Goran Stemme. "A method for tapered deep reactive ion etching using a modified Bosch process." Journal of Micromechanics and Microengineering 17.5 (2007): 1087.

Sadeqi, Aydin, et al. "Cost-effective fabrication of chitosan microneedles for transdermal drug delivery." 2018 40th annual international conference of the IEEE engineering in medicine and biology society (EMBC). IEEE, 2018.

Extended European Search Report in European Application No. EP22808379.

* cited by examiner

Magnification: 35 x

Solid matrix loaded with drug        Solid matrix after drug release

Microneedle loaded with drug    ● Drug    ◯ Solid matrix    ◯ Void

Thick back substrate
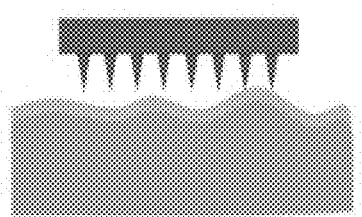 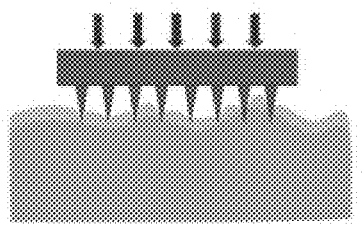 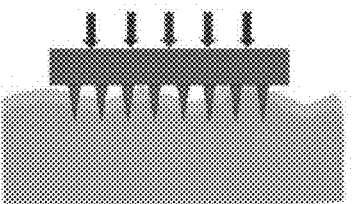
FIG. 26A
Thin elastic back substrate
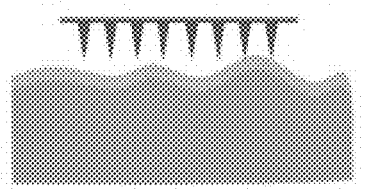 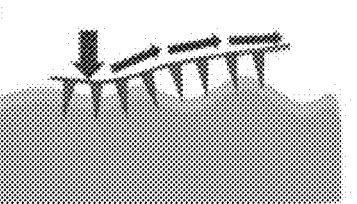 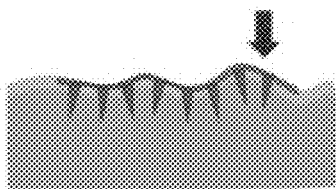
FIG. 26B Stratum Corneum
Epidermis
Dermis
Hypodermis Back substrate
MacroPoSH Microneedle
Langerhans cells
Surface vascular plexus
Lymphatic vessels
Dendric cells
Deep vascular plexus

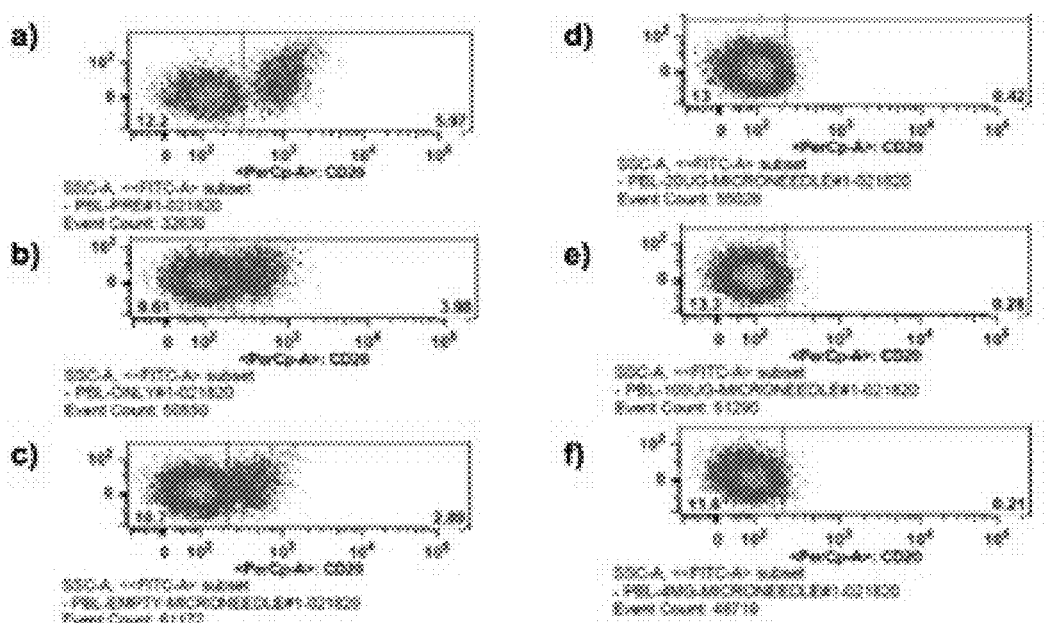
FIG. 29 A-F
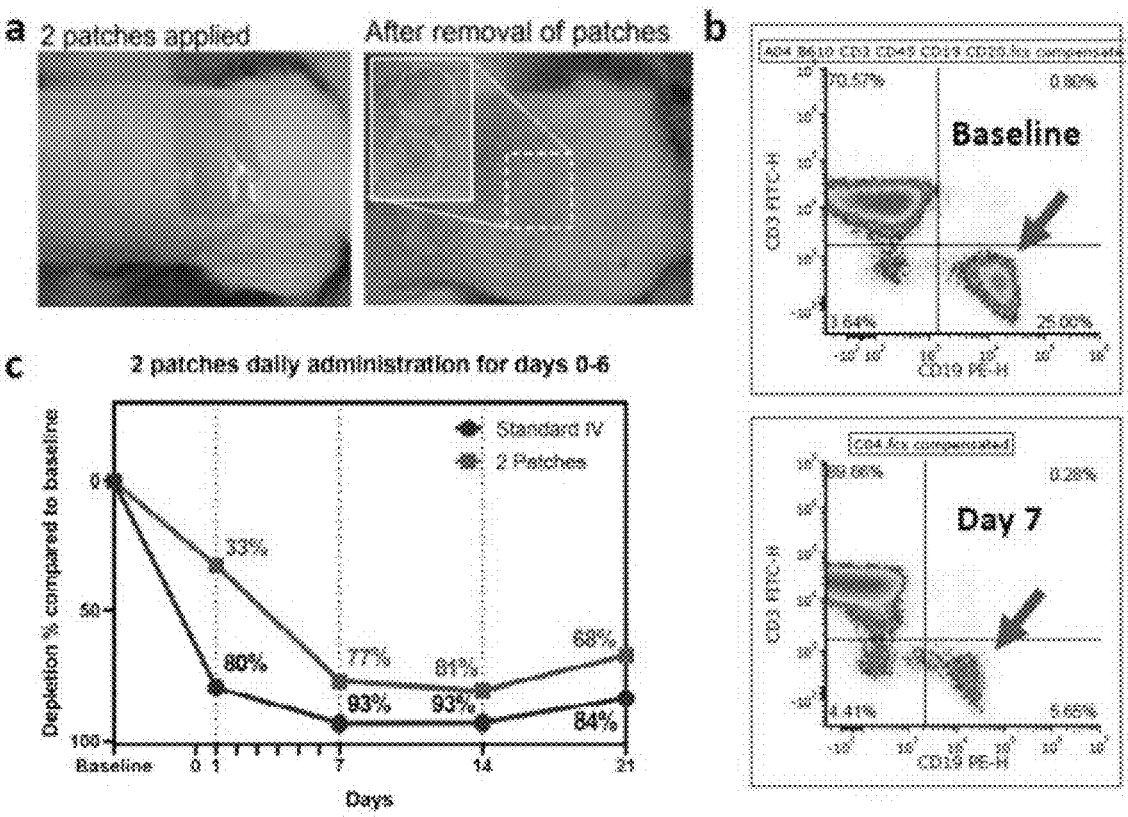
FIG. 30 A-C

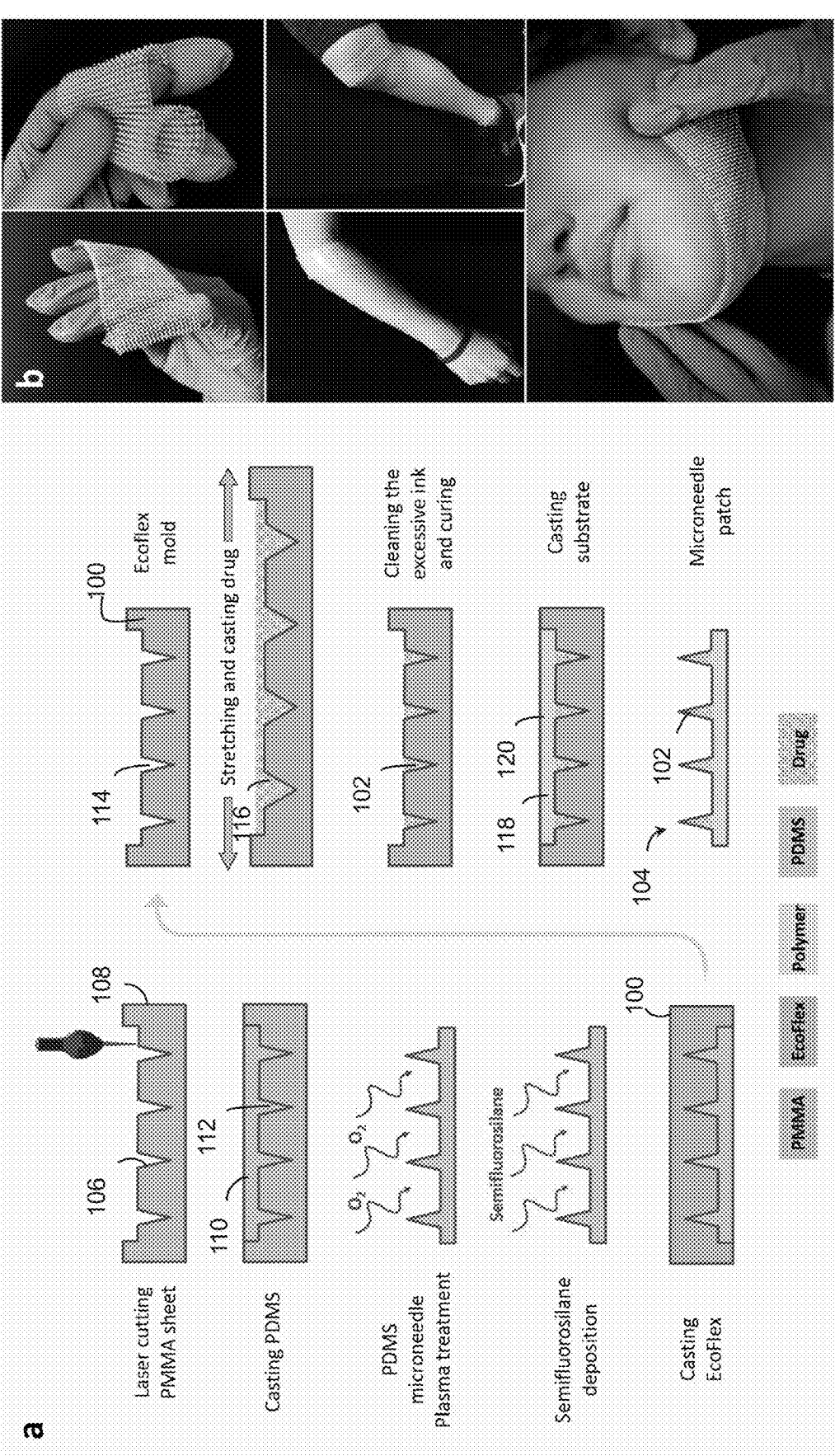
FIG. 34 A-B

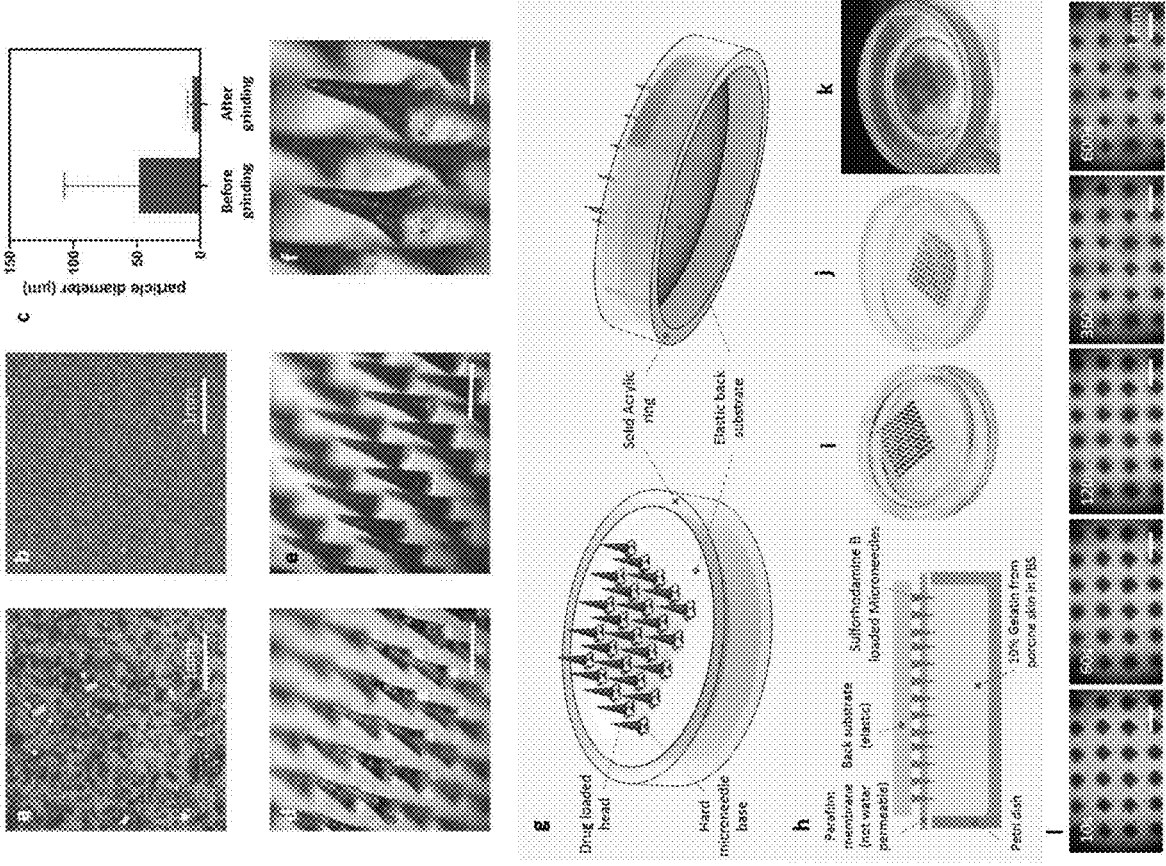
Figure 35 A-L

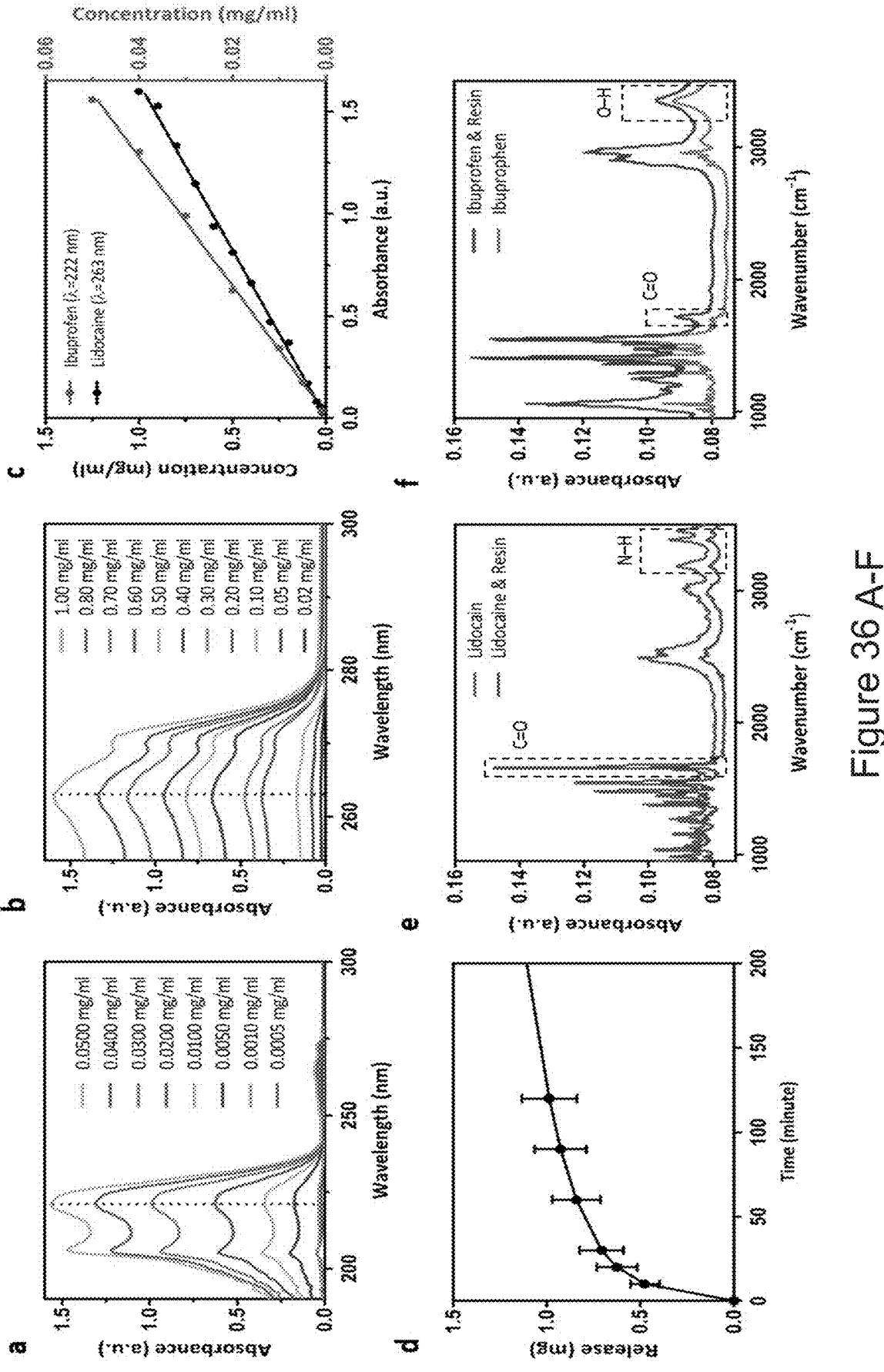
Figure 36 A-F

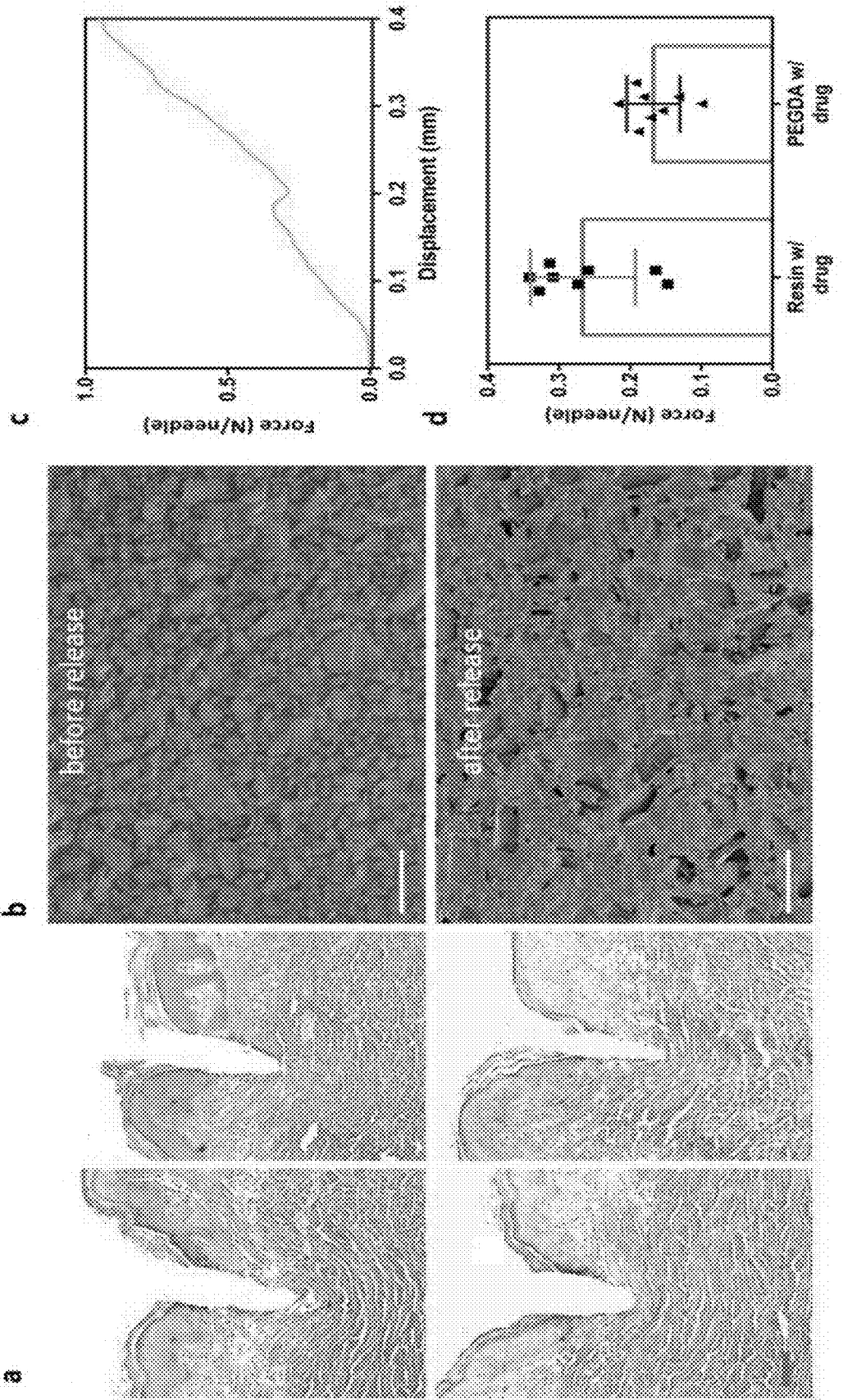
Figure 37 A-D

MACROPOROUS SOLID HARD MICRONEEDLES WITH EMBEDDED PARTICULATE DRUGS

CROSS-REFERENCE TO RELATED APPLICATIONS

This application is a continuation of PCT/US2022/029078, filed May 12, 2022, which is related to, and claims priority to U.S. Provisional Patent Application Nos. 63/201,812, filed May 13, 2021, and 63/212,586, filed Jun. 18, 2021. The entire contents of these applications are incorporated by reference herein.

STATEMENT REGARDING FEDERALLY SPONSORED RESEARCH

This invention was made with government support under grant HU0001-20-2-0014 awarded by the Department of Defense. The government has certain rights in the invention.

BACKGROUND

The present application generally relates to drug delivery systems and methods and relates in particular to autonomous drug delivery systems and methods.

Many systemic drugs require administration by injection, e.g., intravenous, intramuscular, or subcutaneous injection. This is also true of certain therapeutic agents, e.g., vaccines, and diagnostic agents, e.g., radiographic contrast. Administration by injection is often required for drugs with poor or unpredictable absorption by mouth or other routes. This is typically the case with high-molecular-weight drugs, e.g., proteins, e.g., therapeutic monoclonal antibodies, because they are degraded by the oral route and not absorbed. Some low-molecular-weight drugs, such as propranolol, morphine, vancomycin, and tetrahydrocannabinol (THC) are also poorly or inconsistently absorbed by the oral route. First-pass metabolism interferes with the oral absorption of many drugs.

Administration by injection is painful and often requires the services of a healthcare provider, which is expensive and inconvenient. Many drugs administered by injection are provided in aqueous formulation, which can render them less stable, requiring inconvenient shipping and storage conditions, and shortening shelf life.

To solve the foregoing problem, there has been much interest in delivering drugs across the skin, e.g., transdermally. Transdermal administration remains relatively uncommon, however, due to a technical challenge: the epidermis—and particularly the most superficial layer thereof, i.e., the stratum corneum—is a formidable barrier to molecules weighing more than about 500 Daltons, and those with certain physicochemical properties, e.g., high hydrophilicity or hydrophobicity.

One technical approach to deliver a drug past the epidermis for transdermal absorption is to use drug-loaded, skin-penetrating microneedles. Generally, these microneedles comprise: (1) a rigid structure with an apex adapted to pierce into the skin; and (2) a drug active ingredient, typically combined with one or more excipients.

Microneedles offer a convenient transdermal delivery route with potential for long-term sustained release of drugs. Microneedles have received attention as a way to avoid degradation of drugs in the gastrointestinal tract, first-pass effects of the liver associated with oral delivery, and the pain and inconvenience of intravenous injection. Also, using microneedles has offered a minimally invasive, less painful, and self-administrable delivery of drugs from cosmetics to vaccinations which has made microneedles even more attractive. There are numerous complexities to the different fabrication methods for microneedles including UV lithography, drawing lithography, deep X-ray lithography, micro-milling, deep reactive ion etching (DRIE), wet etch technology, and 2D and 3D printing. There are efforts to simplify the manufacturing methods of microneedles, and to make the fabrication process more cost-effective and less time consuming.

Microneedles may be categorized, e.g., as solid, hollow, dissolving, merged-tip, and porous. Porous microneedles have a large volume of distributed pores. However, those known in the art are fragile. Moreover, it has been a challenge to make hard porous microneedles that are strong enough to penetrate skin. Furthermore, most other current microneedle technologies (e.g., hydrogel microneedles) do not have mechanical properties for reliable and stable skin penetration. Moreover, most microneedles can only carry limited amounts of drug. This limitation is particularly problematic for drugs requiring excipients, especially solvents. It is also problematic for drugs that require high absolute doses (e.g., high-molecular-weight drugs, low-potency drugs, antibiotics). Some types of microneedles are physically or chemically incompatible with some drugs.

There remains a need, therefore, for an efficient and economical drug delivery system. More specifically, there is a need for improved microneedle drug delivery systems and methods for fabricating microneedle drug delivery systems.

BRIEF DESCRIPTION OF THE DRAWINGS

FIG. 15 shows schematic representations of a solid matrix loaded with drug and the solid matrix after release of the drug, according to an embodiment of the present disclosure.

FIG. 16 illustrates a bandage with light emitters and light sensors, according to an embodiment of the present disclosure.

FIG. 26*a* is a schematic representation of penetration of microneedles, on a thick back substrate, into a subject, according to an embodiment of the present disclosure.

FIG. 26*b* is a schematic representation of penetration of microneedles, on a thin back substrate, into a subject, according to an embodiment of the present disclosure.

FIGS. 29*a*-29*f* show flow cytometry data for CD20+ cell fluorescence for six samples, according to the present disclosure.

FIG. 30*a* shows two applied patches on an African green monkey for transdermal drug delivery and the area after removal of the patches, according to the present disclosure.

FIG. 30*b* shows flow cytometry data from animals that received daily administration of Rituximab with two patches, according to the present disclosure.

FIG. 30*c* shows B-cell depletion in blood following IV dosing and patch administration of Rituximab, according to the present disclosure.

FIG. 34*a* is a schematic representation of methods for fabricating a microneedle mold, microneedles, and a microneedle patch, according to the present disclosure.

FIG. 34*b* shows the microneedle patch, according to the present disclosure.

FIG. 35*a* shows unground sulforhodamine B particles, according to the present disclosure.

FIG. 35*b* shows ground sulforhodamine B particles, according to the present disclosure.

FIG. 35*c* shows the particle size distribution of sulforhodamine B particles before and after grinding, according to the present disclosure.

FIG. 35*d* shows microneedles made with unground sulforhodamine B particles (scale bar of 1 millimeter), according to the present disclosure.

FIG. 35*e* shows microneedles made with ground sulforhodamine B particles (scale bar of 1 millimeter), according to the present disclosure.

FIG. 35*f* shows microneedles made with ground sulforhodamine B particles with a base structure (scale bar of 0.5 millimeters), according to the present disclosure.

FIG. 35*g* shows schematic representations of microneedle arrays with an elastic back substrate and a solid acrylic ring, according to the present disclosure.

FIG. 35*h* is a schematic representation of an in vitro release experiment, according to the present disclosure.

FIG. 35*i* shows a front side of a dye-loaded microneedle patch, according to the present disclosure.

FIG. 35*j* shows a back side of the dye-loaded microneedle patch of FIG. 35*i*, according to the present disclosure.

FIG. 35*k* shows release of the dye from the dye-loaded microneedle patch of FIGS. 35*i-j*, according to the present disclosure.

FIG. 35*l* shows the release distribution of the dye from the dye-loaded microneedle patch in gelatin at different timestamps, according to the present disclosure.

FIG. 36*a* shows UV-Vis spectra of ibuprofen at different concentrations in solution, according to the present disclosure.

FIG. 36*b* shows UV-Vis spectra of lidocaine at different concentrations in solution, according to the present disclosure.

FIG. 36*c* shows calibration curves for ibuprofen and lidocaine, according to the present disclosure.

FIG. 36*d* is a release profile for ibuprofen/resin and lidocaine/resin microneedle patches in Dulbecco's phosphate-buffered saline (DPBS) with each patch having one hundred microneedles, according to the present disclosure.

FIG. 36*e* shows FTIR absorbance spectra of lidocaine powder compared with lidocaine encapsulated in a microneedle, according to the present disclosure.

FIG. 36*f* shows FTIR absorbance spectra of ibuprofen powder compared with ibuprofen encapsulated in a microneedle, according to the present disclosure.

FIG. 37*a* shows micrographs of histologic sections of pig skin treated with the microneedles (scale bar of 100 micrometers), according to the present disclosure.

FIG. 37*b* shows the surface morphology of resin/drug before release and after release (scale bar of 200 micrometers), according to the present disclosure.

FIG. 37c shows a graph of the mechanical behavior of an individual microneedle containing drug and resin, according to the present disclosure.

FIG. 37d is a bar graph comparing the robustness of the resin/drug microneedle of the present disclosure with a polyethylene glycol diacrylate (PEGDA)/drug microneedle, according to the present disclosure.

DETAILED DESCRIPTION

Figure 1:
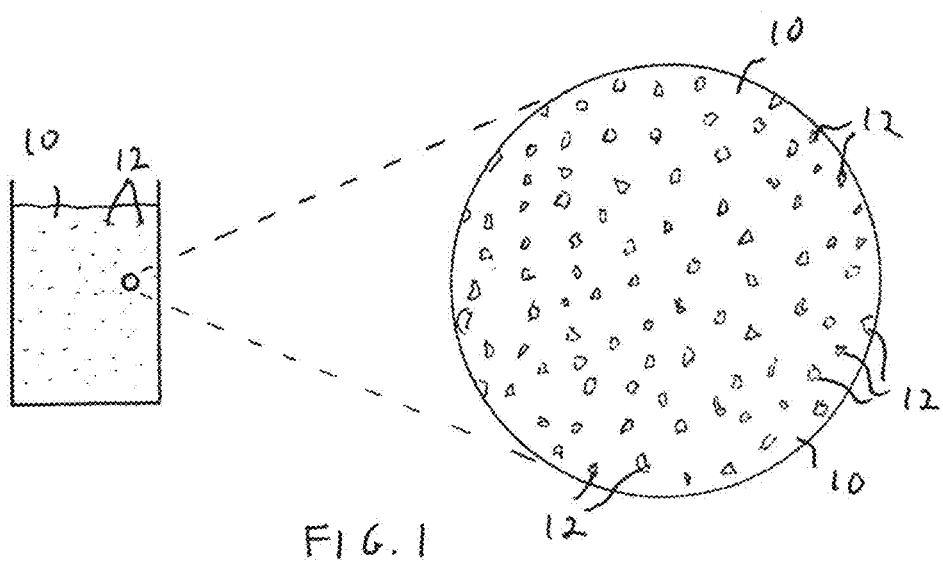
FIG. 1 illustrates a flowable material with a drug in particulate form, according to an embodiment of the present disclosure.
Figure 2:
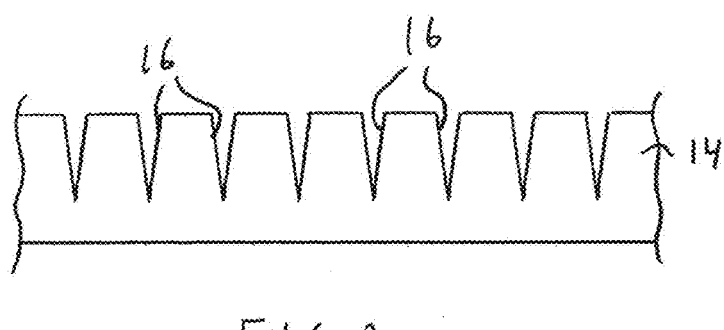
FIG. 2 illustrates a mold having cavities, according to an embodiment of the present disclosure.

Applicants have discovered a drug delivery system comprising one or more microneedles wherein a drug is incorporated in particulate form. When the one or more of the microneedles is applied to the skin of a subject, the drug diffuses through the skin and is delivered, e.g., to the systemic circulation or desired local tissues. Without wishing to be bound by theory, in some embodiments, the solvent to support diffusion of the drug is provided, either totally or substantially, by the interstitial fluid of the recipient subject. Thus, one of several features that distinguishes the present invention is that the drug can be optionally provided in a solid (or substantially solid) form that is adapted for solvation by the skin. Thus, the drug can be provided in the formulation without (or substantially without) a solvent, e.g., without water. Thus, very large amounts of a drug active ingredient (i.e., drug substance) can be loaded into a microneedle (as measured on the basis of drug substance mass per microneedle mass, or active ingredient mass per microneedle volume), for example 10 micrograms or more of drug substance per 35 nanoliter (approximate volume of 1 microneedle). This confers several crucial benefits, e.g., the ability to deliver active ingredients by microneedle that hitherto could not be loaded in sufficient amount on a microneedle; the ability to deliver high-molecular-weight molecules, e.g., biologics, e.g., therapeutic monoclonal antibodies; the ability to create microneedle patches that can require shorter application time and/or less frequent reapplication; and the ability to obtain very high drug concentrations in the vicinity of the microneedle(s), thereby creating a high concentration gradient and correspondingly improved drug delivery. Furthermore, the present invention optionally allows drug to be incorporated into a microneedle without water; this can beneficially increase and extend the stability, e.g., shelf life, of many drugs, including stability at room temperature.

The inventive microneedles also possess remarkable physical characteristics that confer practical benefits. The size and other physical properties of the drug particles can be modulated to change the microneedles' drug delivery characteristics, e.g., drug delivery rate. The composition and structure of the microneedle provide excellent penetration into skin as well as structural integrity, e.g., rigidity or semi-rigidity and resistance to breakage.

Overview of Microneedle Structure and Fabrication

In one aspect, the system includes one or more microneedles, each microneedle comprising a porous material, wherein the porous material comprises the drug in particulate form, optionally free or solvent, substantially free of solvent, free of water and/or substantially free of water.

In some embodiments, the porous material is formed from a flowable material (e.g., a resin that is later cured to form a solid, e.g., a polymer; or a flowable metal, e.g., an alloy, that is later cooled to form a solid). In some embodiments, the flowable material is cast onto a mold comprising one or more needle-shaped mold cavities. Solidification of the flowable material in the mold yields the inventive microneedle(s). In some embodiments, the mold comprises an array of needle-shaped mold cavities in a specific geometric configuration.

Drug Particulates

In some embodiments, drug particulates are combined with the flowable material to obtain a dispersion. In some embodiments wherein the drug particulates comprise a solid, the solid is insoluble or substantially insoluble in the flowable material. Thus, in some embodiments, hydrophobic drug particulates are combined with a hydrophilic flowable material. In some embodiments, hydrophilic drug particulates are combined with a hydrophobic flowable material. In some embodiments wherein the drug is provided in liquid droplets (or micelles, vesicles, or other aggregations of drug in the liquid phase), the droplets (or other such aggregations) are immiscible or substantially immiscible in the flowable material. For purposes of this disclosures, "immiscible" or "substantially immiscible" refer to miscibility under chosen manufacturing conditions, e.g., temperature; thus, two materials can be immiscible for purposes of the invention even if they are miscible under other conditions, e.g., higher temperature, or in the presence of an additive, e.g., an emulsifier.

Drug particulates for use in the present invention can be obtained, for example, by lyophilization, spray drying, or liquid emulsion or microfluidic drop generation followed by solvent evaporation, e.g., dehydration to create drug particles that are later dispersed throughout the flowable material as drug particulates. In some embodiments the size (i.e., largest dimension) of a drug particulate is between about 1 and 100 micrometers. In some embodiments the size of a drug particulate is between about 37 and 100 micrometers. In some embodiments the size of a drug particulate is between about 1 micrometer and 37 micrometers. In some embodiments the size of a drug particulate is between about 500 nanometers and 1 micrometer. In some embodiments the size of a drug particulate is between about 100 nanometers and 500 nanometers. In some embodiments the size of a drug particulate is between about 10 nanometers and 500 nanometers. Throughout this disclosure, where the size of a drug particulate is described, it is understood that particulate size can optionally exist as distribution of sizes. Thus, where a particle measure of particle size is provided, this measure can represent the mean or median of a distribution of particle sizes. Thus, in some embodiments, the median size of a drug particulate is between about 1 and 100 micrometers, between about 1 micrometer and 37 micrometers, between about 500 nanometers and 1 micrometer, or between about 100 nanometer and 500 nanometers. Thus, in some embodiments, 90 percent, 95 percent, 99 percent, or 99.9% of drug particulates in a composition are between about 1 and 100 micrometers, between about 1 micrometer and 37 micrometers, between about 500 nanometers and 1 micrometer, or between about 100 nanometer and 500 nanometers; in the foregoing clause, 16 possible pairwise combinations of a percentage and particle size range are disclosed, each combination of which is disclosed herein as though individually recited.

In some embodiments, the drug particulates are solvent-free, substantially solvent-free, or made without solvent. In some embodiments, the drug particulates are water-free, substantially water-free, or made without water. As used herein, "substantially solvent-free" and "made without solvent" each include, without limitation, compositions that include negligible amounts of solvent, e.g., solvent molecules noncovalently bound to a drug particulate. Likewise, as used herein, "substantially solvent-free" and "made without solvent" each include, without limitation, compositions that include negligible amounts of water, e.g., water present in a drug particulate that is a hydrate, or water passively absorbed or adsorbed from the atmosphere.

A drug particulate can be homogeneous or heterogeneous. A drug particulate can be physically uniform or can consist of two or more parts. For example, a drug particulate can optionally comprise a central core and a superficial shell; and the superficial shell can, if desired, be selected to optimize physical interactions between the drug particulate and the flowable material. For example, the drug particulate can comprise a central core containing a drug active ingredient surrounded by a protective shell. The protective shell can be adapted to prevent dissolution of the drug in the flowable material. Some examples include: use of a hydrophilic protective shell in a hydrophobic flowable material; use of a hydrophobic protective shell in a hydrophilic flowable material; use of a protective shell to prevent a chemical reaction between the drug active ingredient and the flowable material; or use of a protective shell that possesses an absorbance spectrum that protects the drug active material from photodegradation, e.g., during curing of the flowable material.

A drug particulate can comprise one or more excipients, e.g., binders, buffers, salts, stabilizers, and/or preservatives known in the art. A mixture comprising drug particulates and a flowable material can comprise one or more excipients, e.g., binders, buffers, salts, stabilizers, and/or preservatives known in the art.

A drug particulate can be a single drug particle or a physical cluster of one or more drug particles, including any of the aforementioned shells, excipients, or drug active ingredients.

The use of a particulate form of drug can be of special interest for the delivery of high-molecular-weight drugs. These drugs are typically hydrophilic and soluble in interstitial fluid, e.g., of the skin; thus, they are excellent candidates for use in certain embodiments described above.

A drug particulate or a mixture comprising drug particulates and a flowable material can comprise one or more detectable markers known in the art, e.g., nontoxic dyes such as fluorescein, green fluorescent protein, or a radioactive compound. Such markers are useful for monitoring drug release from the microneedle.

Drugs for Use in the Present Invention

In some embodiments, the drug is a monoclonal antibody (e.g., rituximab), an antibody, a therapeutic peptide, a colony stimulating factor, a low-molecular weight drug, an analgesic (e.g., lidocaine), an anesthetic another drug, or combinations thereof. Applicants have verified the operability of microneedles loaded with, inter alia, the protein rituximab and small molecules lidocaine and ibuprofen after embedding each drug inside of the microneedles (see Examples).

In some embodiments, the drug is an analgesic, anesthetic, anti-Alzheimer's, anti-asthma agent, anti-Parkinsonism, antiallergic, antianginal, antiarrhythmic, antiarthritic, antiasthmatic, antibacterial, antibiotic, anticancer, anticoagulant, anti-depressant, antidiabetic, antiemetic, anti epileptic, antifungal, anti glaucoma, anti-gout, antihistamine, antihyperprolactinemia, antihypertensive, anti-inflamatory, anti-migraine, anti-neoplastic, antiobesity, antiparasitic, anti-protozoal, anti-pyretic, antipsoriatic, antipsychotic, antithrombotic, antiulcer, antiviral, anxiolytic, benign prostatic hypertrophy, bronchodilator, calcium hormone or supplement, cardiotonic, cardiovascular agent, chelator, antidote, chemopreventive agent, contraception, diuretic, dopaminergic agent, gastrointestinal agent, gastroprokinetic, hematopoiesis, hemophilia, hormone, hormone replacement therapy, hypnotic, hypocholesterolemic, hypolipidemic, immunomodulator, immunostimulant, immunosuppressant, immunotherapy, lipid regulating agent, male sexual dysfunction medication, multiple sclerosis, muscle relaxant, neuroleptic, nootropic, anti-osteoportic, phytoestrogen, platelet aggregation inhibitor, prostaglandin, radioenhancer for radiotherapy, muscle relaxant, sedative, tranquilizer, and stimulant, respiratory distress syndrome, vasodilator, or vitamin.

In some embodiments, an inventive microneedle is provided that is loaded with a vaccine in lieu of a drug.

Porous Material

Inventive microneedles, in their finished state, comprise a hard porous material. In some embodiments, the porosities of the porous material are created by spatial exclusion imposed by the presence of drug particulates dispersed in the flowable material during the microneedle manufacturing process. Thus, in some embodiments, the drug particulates are contained within the porosities of the porous material. In some embodiments, the drug particulates occupy substantially all of the volume of the porosities of the porous material. In some embodiments, the drug particulates occupy at least 50%, 60%, 70%, 80%, 90%, 95%, 97%, 99%, 99.9% or 99.99% of the volume of the porosities of the porous material. In some embodiments, substantially all of the porosities are occupied by drug particulates. In some embodiments, at least 50%, 60%, 70%, 80%, 90%, 95%, 97%, 99%, 99.9% or 99.99% of the porosities are occupied by drug particulates. In some embodiments, substantially all of the solvent-accessible volume of the microneedle is occupied by drug particulates. In some embodiments, at least 50%, 60%, 70%, 80%, 90%, 95%, 97%, 99%, 99.9% or 99.99% of the solvent-accessible volume of the microneedle is occupied by drug particulates. For purposes of this disclosure, "solvent-accessible volume" refers the maximum volume of a suitable solvent, e.g., water, absorbed by a microneedle immersed in that solvent.

In some embodiments, the flowable material may be a biocompatible resin. For example, dental SG resin may be used. Other suitable types of biocompatible resins include, but are not limited to, BioMed Clear Resin (RS-F2-BMCL-01), Biomed Amber Resin (RS-F2_BMAM-01), Dental LT Clear Resin (RS-F2-DLCL-02), Surgical Guide Resin (RS-F2-SGAM-01), and Dental SG resin (RS-F2-DGOR-01). The biocompatible resin may be photo-curable and, thus cured, yield a hard polymer. In some embodiments, the biocompatible resin or its cured product may include a species selected from chitosan, chitosan polybutylene adipate terephthalate, poly(butylene adipate-co-terephthalate), polyethylene glycol, poly(ethylene glycol) diacrylate, gelatin, gelatin methacyloyl, polyvinyl alcohol, silk, and combinations thereof. Other materials used to fabricate the porous microneedles may include, but are not limited to, polylactic acid (PLA), polyvinyl alcohol (PVA), poly(ethylene glycol diacrylate) (PEGDA), or UV curable polymers.

In some embodiments, a porous material is first obtained in the absence of drug particulates, and the drug particulates are later introduced into the porous material. Inherently porous materials are known in the art (polymers including PLGA, PVA, PDMS, acrylics, and hydrogels including PEG gelatin, chitosan); or porous material can be created by combination of a sacrificial material with a flowable material, wherein the two are immiscible or insoluble (as the case may be for the phase of the sacrificial material). Once the flowable material has solidified, the sacrificial material can be selectively removed. e.g., by chemical means, to obtain a porous material with open pores. Drug particulates can then be formed within the porous material, for example by saturating the porous material with a carrier liquid comprising the drug, followed by evaporation or sublimation of the carrier liquid, leaving drug particulates in the porous material. In some embodiments, the drug may be water-soluble and the porous material may be hydrophobic, or the drug may be lipid-soluble and the porous material may be hydrophilic. For purposes of this disclosure, a "sacrificial material" refers to a material that is used during a manufacturing process or portion thereof but removed before the finished product is obtained, for example, to leave a void or a cavity.

Whether the porosities are created by spatial exclusion imposed by the presence of drug particulates dispersed in the flowable material or first obtained in the absence of drug particulates, the porosities should be interconnected in such a way that all or substantially all of the drug particulates are accessible to an external solvent e.g., interstitial fluid. This accessibility may be referred to herein as creating open pores or available drug.

Microneedle Structure

Herein disclosed, inter alia, is a new class of microneedles called macroporous structured hard microneedles (macroPoSH). MacroPosh microneedles are hard microneedles with a highly porous structure, with micro/nano size pores that can facilitate loading of very high amounts of drug onto the microneedles. At the same time, the MacroPosh needles disclosed herein possess excellent structural properties. The fabricated microneedles are resistant to breakage, having a high Young's modulus (expected 1000 times higher than human skin) and can effectively penetrate a variety of skin types without breaking. The microneedles can form and maintain an exceptional sharp tip (see Examples).

Figure 9:
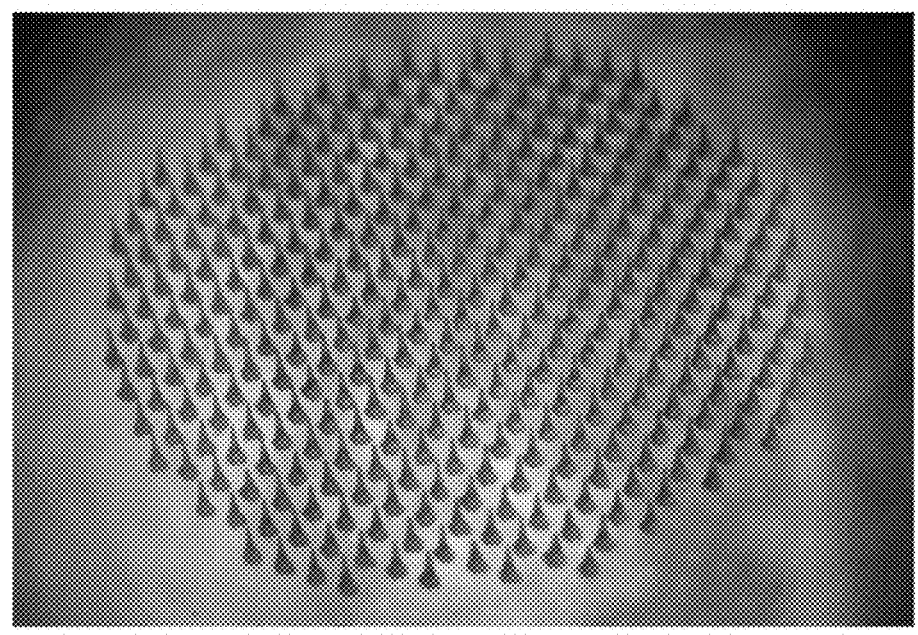
FIG. 9 illustrates an array of microneedles, according to the present disclosure.
Figure 10:
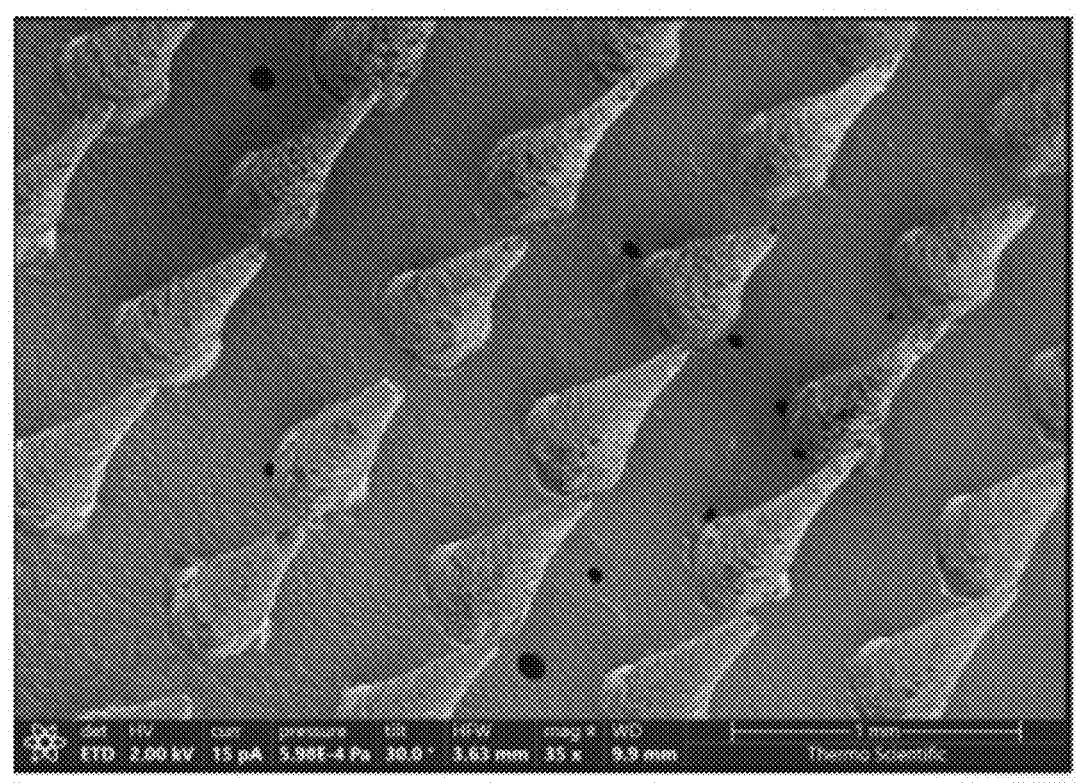
FIG. 10 shows a scanning electron micrograph of microneedles, according to the present disclosure.
Figure 11:
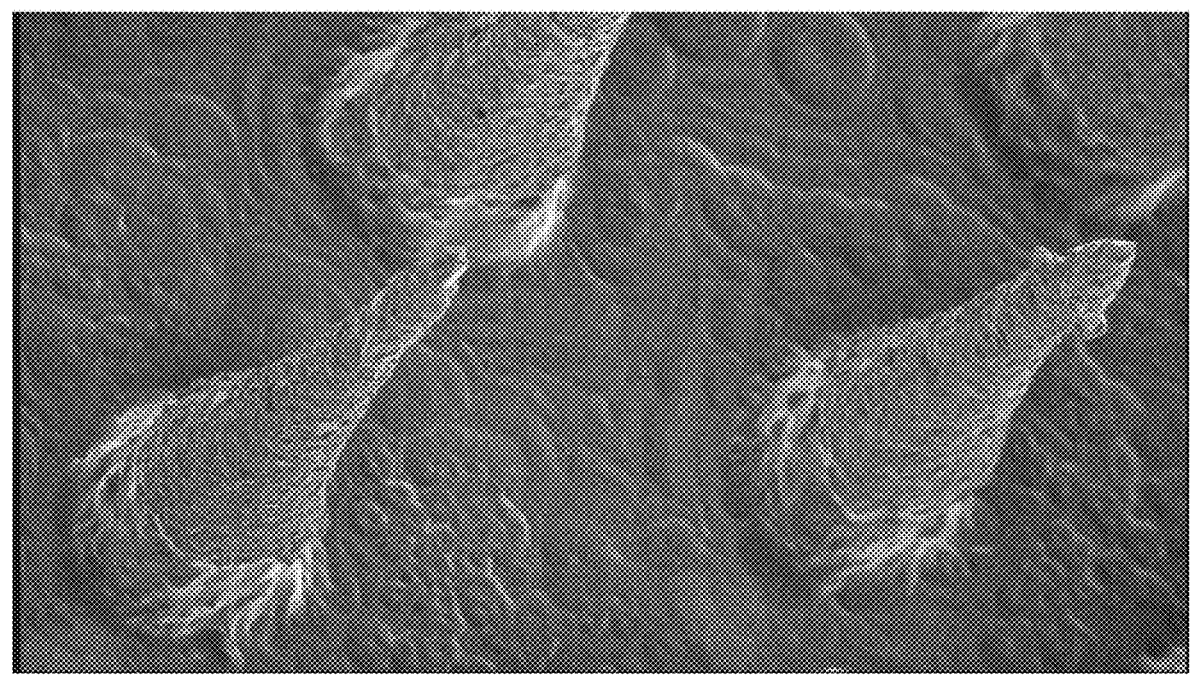
FIG. 11 is an enlarged view of a few of the microneedles of FIG. 10, according to the present disclosure.
Figure 12:
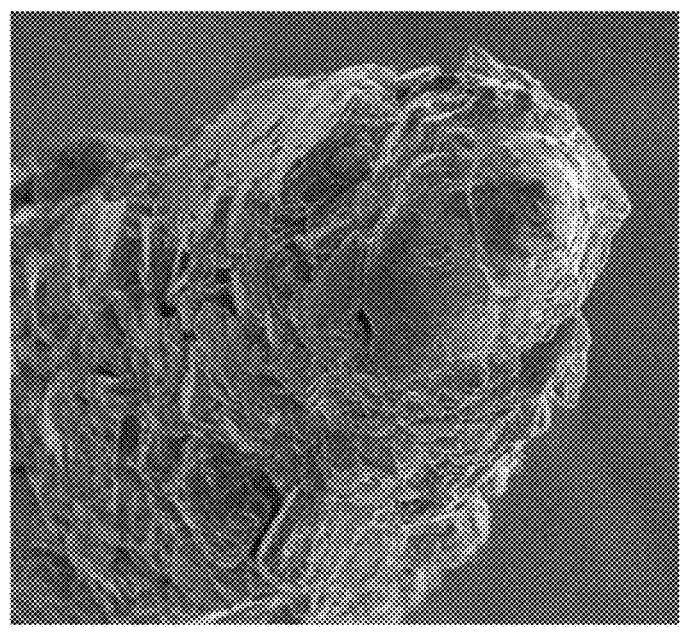
FIG. 12 is a further enlarged view of a portion of a microneedle of FIG. 10, according to the present disclosure.

FIG. 9 shows an array of microneedles of an aspect of the invention, and FIG. 10 shows a scanning electron micrograph of a portion of a microneedle of an aspect of the present invention prior to release of the drug. FIG. 11 shows an enlarged view of a few of the microneedles of FIG. 10, and FIG. 12 shows a further enlarged view of a portion of a microneedle of FIG. 10.

The pore sizes of the microneedles may be correlated with the size of the drug powder loaded into the microneedles. The size of the pores may be of any dimension from nano-scale to micro-scale. For instance, the pores may have diameters ranging from about 100 nanometers to about 40 micrometers. In one specific embodiment, drug particulates having a size of about 6 micrometers provides pore sizes of about 6 micrometers. In some embodiments the pores can range from about 100 nanometers to 100 micrometers in the largest dimension. In some embodiments the pores can range from about 10 to 100 micrometers. In some embodiments the pores can range from about 1 to 100 micrometers. In some embodiments the pores can range from about 500 nanometers to 10 micrometers. In some embodiments the pores can range from about 500 nanometers to 50 micrometers.

In some embodiments, the axial length of the microneedle (i.e., as measured from the apex [i.e., sharp point] to the base) is between 0.5 and 10 mm. In some embodiments, the axial length is between 0.5 and 8 mm. In some embodiments, the axial length is between 0.5 and 6 mm. In some embodiments, the axial length is between 0.5 and 5 mm. In some embodiments, the axial length is between 0.5 and 4 mm. In some embodiments, the axial length is between 0.5 and 3 mm. In some embodiments, the axial length is between 0.5 and 2 mm. In some embodiments, the axial length is between 0.5 and 1.5 mm. In some embodiments, the axial length is between 0.5 mm and 1 mm. In some embodiments, the axial length is between 1 mm and 1.5 mm. In some embodiments, the axial length is between 0.75 mm and 1 mm. In some embodiments, the axial length is between 1 mm and 1.25 mm. In some embodiments, the axial length is between 0.8 mm and 1.2 mm. In some embodiments, the axial length is between 0.9 mm and 1.1 mm. In some embodiments, the axial length is between 0.1 mm and 1 mm. In some embodiments, the axial length is between 0.1 mm and 0.75 mm. In some embodiments, the axial length is between 0.1 mm and 0.5 mm.

Back Substrate

Figure 5:
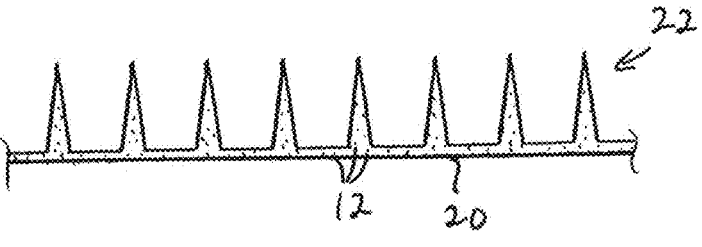
FIG. 5 illustrates a cured polymeric material having microneedles after removal from the mold, according to an embodiment of the present disclosure.

The material attached to the base(s) of one or more microneedles for supportive purposes, e.g., to provide an adhesive backing and/or to position multiple microneedles in an array, is herein referred to as the back substrate. In some embodiments, the back substrate can be, or can comprise, a thin elastic (FIG. 26B). In some embodiments, the back substrate can be, or can comprise, a flexible adhesive. In some embodiments, the back substrate can be, or can comprise, a woven material. In some embodiments, the back substrate can be, or can comprise, a film. In some embodiments, the back substrate can be, or can comprise, a bandage or dressing. In some embodiments, the back substrate can be, or can comprise, a biodegradable material. In some embodiments the back substrate can act as an intermediate adhesive to a larger patch for clinical application. In some embodiments the back substrate can be a continuation of the same porous material comprising the microneedles (FIG. 5). In some embodiments the back substrate can be a secondary, drug-loaded material, including a drug-loaded porous material.

A polymer that makes a strong bond with the microneedles may be used as a material form the back substrate. The material used to form the back substrate may be rigid or flexible depending on the application. Suitable flexible materials include, but are not limited to, paper, textile, polyether ether ketone (PEEK), polyethylene terephthalate (PET), polyethylene naphthalate (PEN), polytetrafluoroethylene (PTFE), parylene, and polyimide. Elastic and flexible resins may also be used (e.g., Elastic 50A Resin (Part Number: FLELCL01), Flexible 80A Resin (Part Number: FLFL8001)). UV curable resins may also be used, such as when there is a need for conformality, flexibility, and elasticity in the microneedle patch. Hard resins may be used for applications having a need for rigid back substrates. A suitable example of a hard resin includes, but is not limited to, Surgical Guide Resin (Part Number: FLSGAM01).

In some embodiments, wherein the back substrate is planar or substantially planar, the "planar area" of the patch can be calculated as the area of the patch in the plane defined by the back substrate. In some such embodiments, the "microneedle planar area" of the patch can be calculated as the area of a regular or irregular polygon, wherein the polygon is defined as that having the largest area circumscribed by the locus of all lines: (1) in the plane of the back substrate and (2) that connect all microneedles in pairs. Stated more plainly, but without wishing to modify the foregoing geometric definition, the microneedle planar area is the area defined by the perimeter of the microneedles on the patch. In some embodiments, the planar area of the patch is about 0.5, 1, 2, 3, 4, 5, 6, 7, 8, 9, 10, 12, 15, 16, 18, 20, 24, 25, 27, 28, 30, 32, 33, 35, 36,40, 42, 45, 48, 50, 55, 56, 60, 63, 64, 65, 70, 72, 75, 80, 81, 85, 90, 95, 99, 100, 105, 110, 120, 121, 125, 130, 135, 140, 144, 145, 150, 160, 170, 180, 190, 200, 210, 215, 220, or 225 cm$^2$. In some embodiments, the planar microneedles area of the patch is about 0.1, 0.2, 0.25, 0.3, 0.4, 0.5, 1, 2, 3, 4, 5, 6, 7, 8, 9, 10, 12, 15, 16, 18, 20, 24, 25, 27, 28, 30, 32, 33, 35, 36,40, 42, 45, 48, 50, 55, 56, 60, 63, 64, 65, 70, 72, 75, 80, 81, 85, 90, 95, 99, 100, 105, 110, 120, 121, 125, 130, 135, 140, 144, 145, 150, 160, 170, 180, 190, 200, 210, 215, 220, or 225 cm$^2$. In some embodiments, the planar area of the patch is between about 0.1 and 1, 1 and 5, 1 and 10, 5 and 10, 10 and 20, 10 and 100, 20 and 50, 50 and 100, 100 and 150, 150 and 200, or 200 and 250 cm$^2$. In some embodiments, the planar microneedle area of the patch is between about 0.1 and 1, 0.5 and 100, 1 and 5, 1 and 10, 5 and 10, 10 and 20, 10 and 100, 20 and 50, 50 and 100, 100 and 150, 150 and 200, or 200 and 250 cm$^2$.

Microneedle Fabrication

Figure 3:
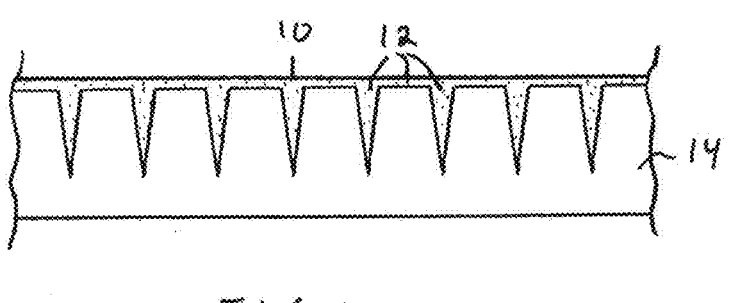
FIG. 3 illustrates the flowable material with the drug in particulate form of FIG. 1 cast onto the mold of FIG. 2, according to an embodiment of the present disclosure.

One example of a process to make inventive microneedles is set forth in FIGS. 1 through 6. FIG. 1 shows a flowable material 10, such as a resin, in which is dispersed a drug in particulate form 12 (better seen diagrammatically in the enlarged area of FIG. 1). The material 10 is cast onto a mold 14 comprising cavities 16 shown in FIG. 2. As shown in FIG. 3, the material 10 with the drug 12 fills the cavities. The drug may be provided in a particulate form, such as a powder. The combination of the flowable material and drug in particulate or solution form is herein referred to as a casting paste or a casting solution, respectively. It has further been discovered that the finer the powder gets, when using the particulate form, the less amount of resin is required to create a usable casting paste that results in a porous material with mechanical properties robust enough to achieve dermal penetration and removal without microneedle fracture (See Example [0145]). As an example, for a powder of 10 micron or larger particles, one can mix 1:1 (w/w) ratio of drug powder to resin to create a castable paste with robust mechanical properties, once cured. If the size of particles is decreased (for example, from 10 micron to 1-5 micron (this can translate to longer grinding time, or an optimized spray drying method), the drug powder and resin may be mixed together with 2:1, 3:1, 4:1, 5:1 and even 6:1 (w/w—drug/resin) ratios without overly compromising mechanical properties, such that the microneedles retain enough rigidity to effectively penetrate the skin and structural integrity to remain intact during application, wear time and removal from the skin. This means that finer drug particles, leading to finer drug particulates, allow for a much higher loading capacity for a given volume of microneedles.

Figure 4:
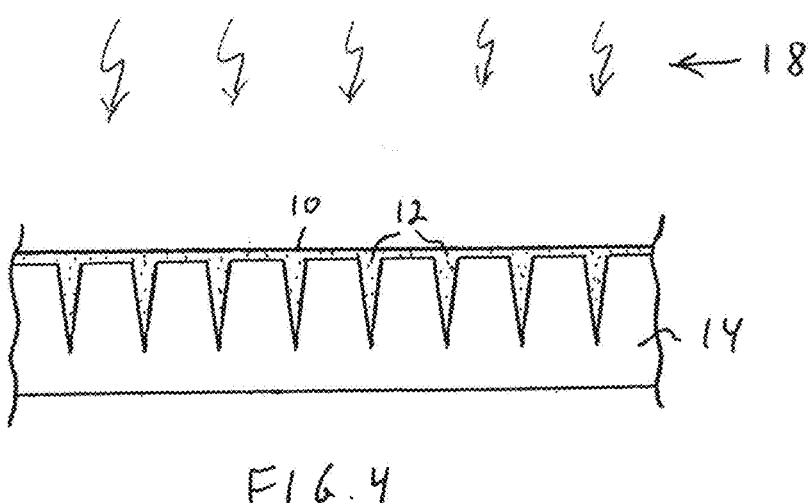
FIG. 4 shows a schematic representation of curing the flowable material in the mold, according to an embodiment of the present disclosure.
Figure 6:
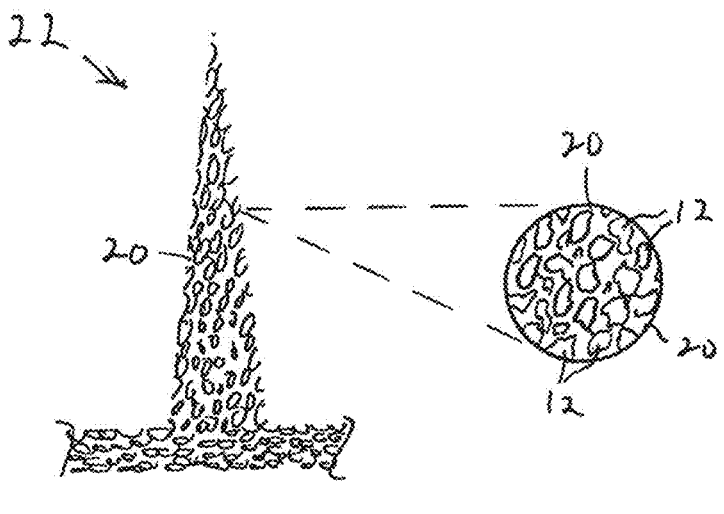
FIG. 6 illustrates a microneedle of the cured polymeric material of FIG. 5, according to an embodiment of the present disclosure.

With reference to FIG. 4, the material 10 with the drug particulates 12 in the mold 14 may be cured using, for example, heat or electromagnetic energy 16 such as UV or visible light. With reference to FIG. 5, the cured polymeric material 20 that still includes the drug particulates 22 may then be removed from the mold, retaining the needle-like shapes 22 from the mold cavities. FIG. 6 shows diagrammatically that the cured polymeric material 20 of each needle 22 includes undissolved (immiscible) drug particulates 12 within the cured polymeric material 20. The cured polymeric material may have a hardness of at least about 40 Shore A. In some embodiments the hardness of the cured polymeric material is between 40 Shore A and 90 Shore D. In some embodiments the hardness of the cured polymeric material is between 40 Shore D and 80 Shore D. In some embodiments the hardness of the cured polymeric material is between 60 Shore A and 80 Shore D. In some embodiments the hardness of the cured polymeric material is between 60 Shore A and 100 Shore A. In some embodiments the hardness of the cured polymeric material is at least about 80 Shore D.

In accordance with various aspects, the invention provides for the fabrication of drug loaded microneedles in accordance with various aspects of the invention. The molds may be formed using cross-over lines (COL) laser lithography to make microneedles that combine the benefits of both hard and soft microneedles as disclosed in WO 2019/203888 published Oct. 24, 2019, the disclosure of which is hereby incorporated by reference in its entirety.

Figure 7:
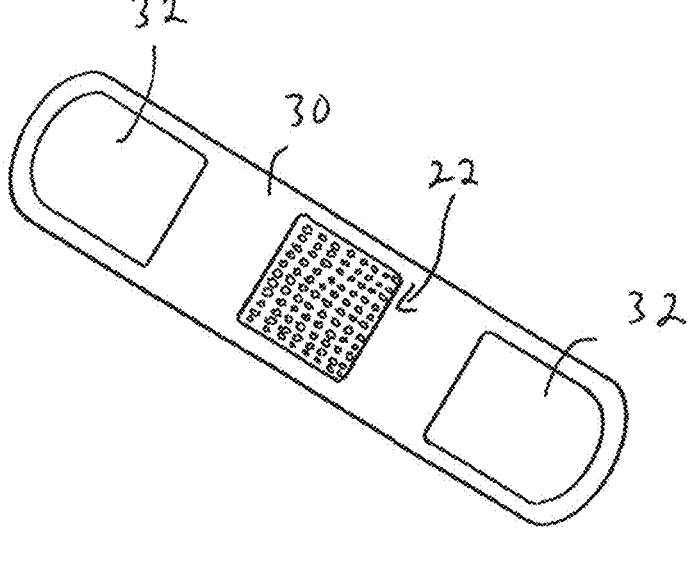
FIG. 7 illustrates a bandage having an array of microneedles, according to an embodiment of the present disclosure.

FIG. 7 shows an array of such microneedles (seen as needle-like shapes or protrusions) 22 used with a bandage 30 that includes adhesive areas 32.

Compared to the state of the art, these microneedles provide unprecedented drug loading capacity. In some aspects, the drug loading capacity may be picograms to milligrams per microneedle, or picograms to grams per patch. The microneedles also provide reliable skin penetration. Significant is the preparation of the drug-loaded casting paste through an innovative dry emulsification of the drug in a powder form into a biocompatible resin (with no solvent or substantially no solvent). The dry drug powder is normally not soluble into the resin. By controlling the size of drug powder particles (to be less than 10 μm) and mixing with, for example, a Class IIa (long-term biocompatible resin with high resistance to fracture) biocompatible solvent free precuring solution at 1:1 (w/w) ratio it is possible to create paste-like dispersion, the casting paste, which can be casted into a mold. In certain aspects, the resin is USP Class VI. Casting and curing of such paste create a porous material. The pores in the hard-cured resin matrix are created either completely or substantially by spatial exclusion imposed by the presence of drug particulates. The pores allow for all or substantially all of the drug particulates to be accessible to an external solvent e.g. interstitial fluid.

Figure 33:
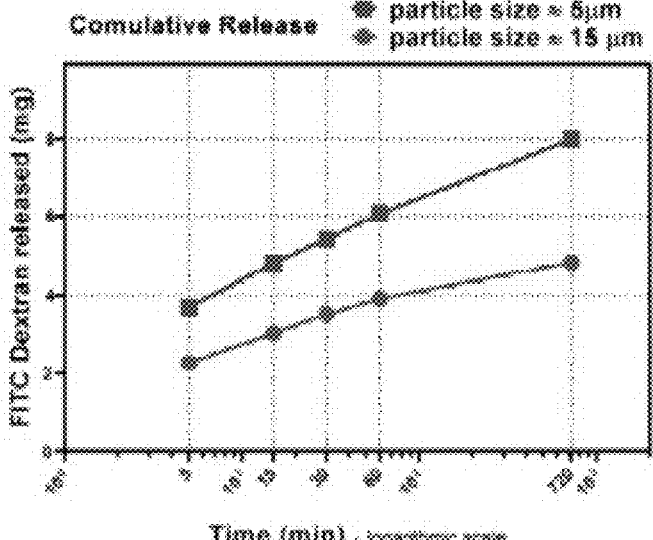
FIG. 33 shows FITC-Dextran release data of two different formulated needle patches, according to the present disclosure.

Controlling the particulate size not only affects the drug loading capabilities, but also has a distinct effect on the delivery rate of the drug (see FIG. 33). Introducing this type of control based on particulate size is a very significant finding to move towards a controlled and sustained drug delivery system that is both efficient and economical (for example, as a single use patch free of electronics). This also leads to the possibility of including varying, defined drug particulate sizes to improve or modulate the drug release profile with or without including any additional modifiers.

Turning to FIG. 34a, some methods of fabricating a microneedle mold 100, microneedles 102, and a microneedle patch 104 in accordance with the present disclosure are shown. Fabrication of the microneedle mold 100 may begin with laser cutting one or more microneedle-shaped depressions 106 into a first material in a crossover line pattern using the cross-over-lines (COL) fabrication procedure (see WO 2019/203888) to provide a first mold 108. A second material may be cast onto the first mold 108 to fill the microneedle-shaped depressions 106 with the second material. Subsequent curing of the second material may provide a second mold 110 having one or more microneedles 112 formed within the microneedle-shaped depressions 106. The cured second mold 110 may be removed from the first mold 108, and a surface of the cured second mold 110 may undergo plasma treatment to activate the surface of the microneedles 112. A release layer may be applied to the plasma treated surface of the cured second mold 110. In one embodiment, the release layer may be a silane layer applied by treatment with trichloro(1H, 1H, 2H, 2H-perfluorooctyl)silane. Following application of the silane layer, a third material may be cast onto the surface of the cured second mold 110, and the third material may be cured to provide the microneedle mold 100 having microneedle-forming cavities 114. The microneedle mold 100 may be removed from the cured second mold 110. In one embodiment, the first material is an acrylic sheet, the second material is a silicone elastomer such as polydimethylsiloxane (PDMS), and the third material is an ultra-elastic silicone rubber such as EcoFlex™.

With continued reference to FIG. 34a, fabrication of the microneedles 102 and the microneedle patch 104 will now be described. The use of an ultra-elastic microneedle mold 100 enables the microneedle mold 100 to be stretched to facilitate embedding a highly viscous drug/biocompatible resin mixture into the mold 100. Additionally, utilizing an ultra-elastic mold may decrease the microneedle fabrication time drastically by avoiding a vacuuming procedure to embed the casting paste into the tiny microneedle needle-forming cavities of the mold. As shown in FIG. 34a, the microneedle mold 100 may be stretched beyond its original size to expand the size of the microneedle-forming cavities 114. A mixture 116 of a drug and a biocompatible resin may be cast on the microneedle mold 100 such that the mixture 116 fills the expanded microneedle-forming cavities 114. The drug in the mixture 116 may be in solid particulate form. In some embodiments the size of the drug particulates is between about 1 and 100 micrometers in the largest dimension. In some embodiments the size of the drug particulates is between about 37 and 100 micrometers in the largest dimension. In some embodiments the size of the drug particulates is between about 1 micrometer and 37 micrometers in the largest dimension. In some embodiments the size of the drug particulates is between about 500 nanometers and 1 micrometer in the largest dimension. In some embodiments the size of the drug particulates is between about 100 nanometers and 500 nanometers in the largest dimension. In some embodiments the size of the drug particulates is between about 10 nanometers and 500 nanometers in the largest dimension.

The microneedle mold 100 may be allowed to contract to its original size, and the biocompatible resin may be cured to provide the microneedles 102. In some embodiments, the biocompatible resin may be photo-cured by exposure to ultraviolet light. In one embodiment, the biocompatible resin is photo-cured by exposure to 405 nanometer (nm) light. The resulting microneedles 102 may be solid and porous with the drug embedded in the pores of the microneedles 102.

An elastic polymer 118 may be cast on the microneedle mold 100 over the microneedles 102 to provide an elastic back substrate 120, as shown in FIG. 34a. Curing the elastic polymer 118 may provide the microneedle patch 104 having the elastic back substrate 120 bonded to the microneedles 102. In some embodiments, the elastic polymer may be photo-cured by exposure to ultraviolet light. The microneedle patch 104 may be removed from the microneedle mold 100.

The use of a hard polymer for the microneedles 102 and an elastic polymer for the back substrate 120 provides the benefits of both stiff and rigid microneedles with guaranteed insertion in tissue, and a soft back substrate with elasticity. A tip of the microneedles may be robust and capable of resisting breakage at applied forces of up to about 0.26 newtons (N). This provides more than a four-fold margin of safety over the force (0.058 N per needle) needed for reliable insertion into skin using microneedles of the same geometry. The conformable back substrate 120 may be configured to conformably adapt to the curvature of skin of any body part for application of the microneedle patch 104 to any body part (see FIG. 34b).

Macroporous, metallic microneedles may also be provided. Here a microneedle mold that may handle molten metal may be fabricated. The mold may be made out of clay, ceramic, or any material that can retain its shape in the presence of molten metal. A molten mixture of two different metals—e.g., metal X and metal Y (gold/silver, zinc/cupper, silver/zinc, steel/titanium or any possible alloy mixture) will be cast to create metallic microneedles. The metallic microneedles will be placed in one of its alloy metals etchants (metal X etchant) to etch that metal (metal X). For example, if a steel/titanium microneedle was formed, in that case the composite would be put into steel etchant to etch the steel away, leaving the titanium in a porous form (the pores being where the steel had been). This will create a highly porous metallic microneedle, which is very hard and can be used for various transdermal and in situ sensing. To use it as drug delivery device, drug in solution form can be dried on the microneedles or fine drug powder can be pressed against the microneedles to load the needles the porosities with drug particulates.

Figure 17:
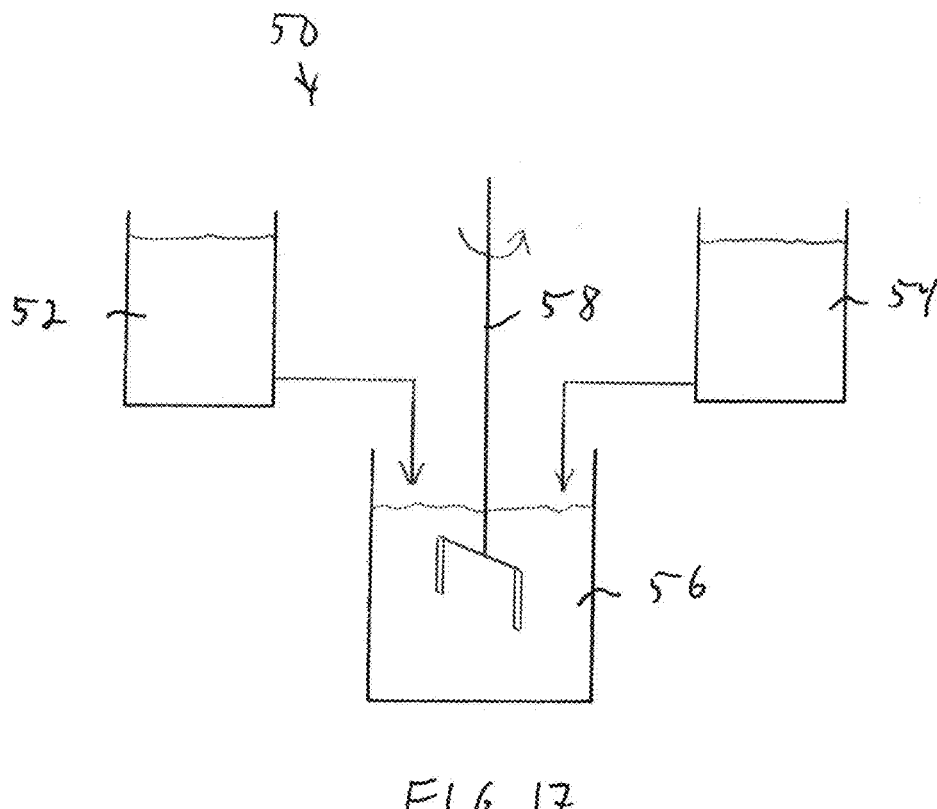
FIG. 17 is a schematic representation of combining two flowable materials to form a composite material, according to an embodiment of the present disclosure.
Figure 18:
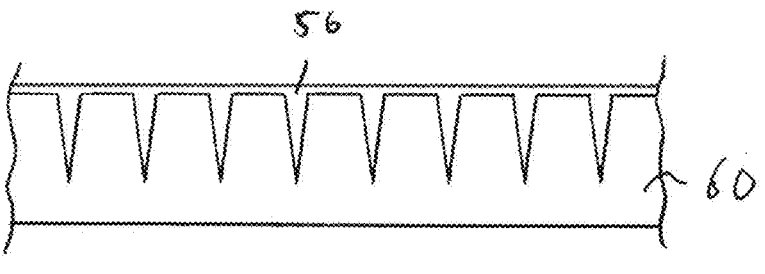
FIG. 18 illustrates the composite material of FIG. 17 cast onto a mold, according to an embodiment of the present disclosure.

FIG. 17 shows at 50 two flowable materials 52, 54 that may be different resins or different metals in liquid or molten form. Where the materials 52, 54 are metal, they may be any of gold, silver, carbon, steel, copper, brass, bronze, titanium, beryllium, aluminum, tin and zinc and alloys thereof. The materials 52, 54 are combined to form a composite material 56 that is mixed, for example, by a mixer 58. The materials 52, 54 are chosen such that they are immiscible but form a heterogeneous mixture capable of being mixed to a state of small droplets (i.e., less than 5 micrometer in diameter). One of the materials is chosen to be sacrificial. With reference to FIG. 18, the composite material 56 is then cast onto a mold 60 (again, for example, as formed in WO 2019/203888 published Oct. 24, 2019, the disclosure of which is hereby incorporated by reference in its entirety.

Figures 19, 20:
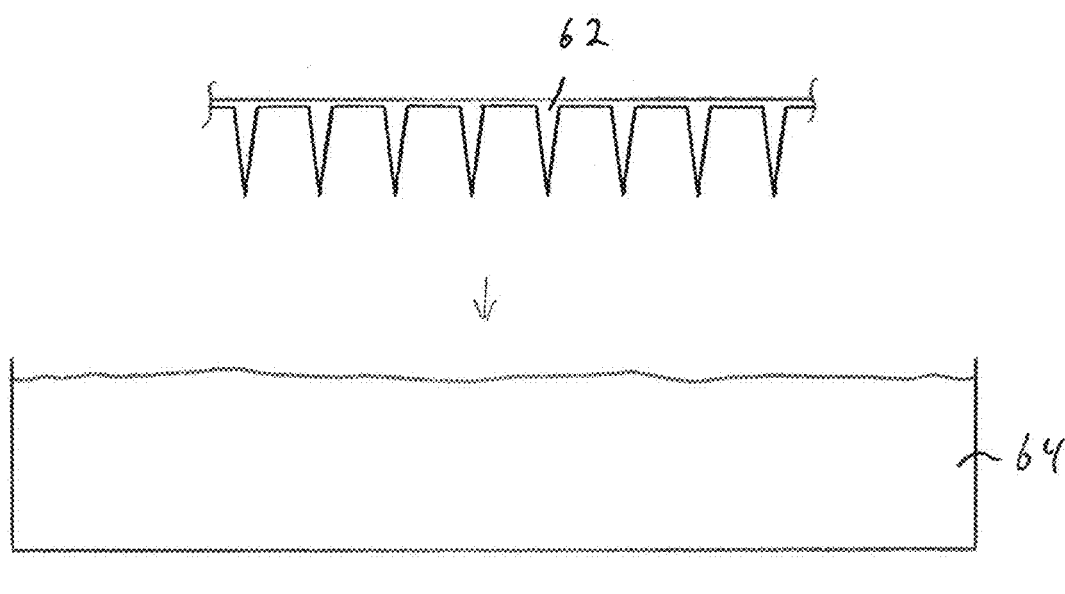
FIG. 19 is a schematic representation of placing the cured composite material of FIG. 18 into an etchant solution, according to an embodiment of the present disclosure.
FIG. 20 is a schematic representation of the cured composite material of FIG. 18 placed into the etchant solution, according to an embodiment of the present disclosure.

The cast composite material is then cooled or otherwise cured (e.g., to a hardness of at least about 20 Shore D), and with reference to FIGS. 19 and 20, it is placed into an etchant solution 64, that is preferably agitated as shown at 66 to cause the sacrificial material (e.g., 54) to be removed. As the materials 52, 54 are chosen such that they are immiscible but are each able to be broken up (e.g., stirred) into small portions, the removal of the sacrificial material is designed (due to mixing and volumetric selection of the materials) to leave a plurality of open pores in the remaining material (e.g., 52). As the etchant must flow to the sacrificial material, the pores will be interconnected, or in fluid communication with one another. For purposes of this disclosure, two compartments are "in fluid communication" if a fluid can flow or diffuse from one of the compartments to the other. Fluid communication can be tested, for example, by filling the compartments with a fluid such as water, placing a dye or marker into a first compartment, and sampling the second compartment for the presence of the dye or marker, which would indicate diffusion between the compartments.

Figure 21:
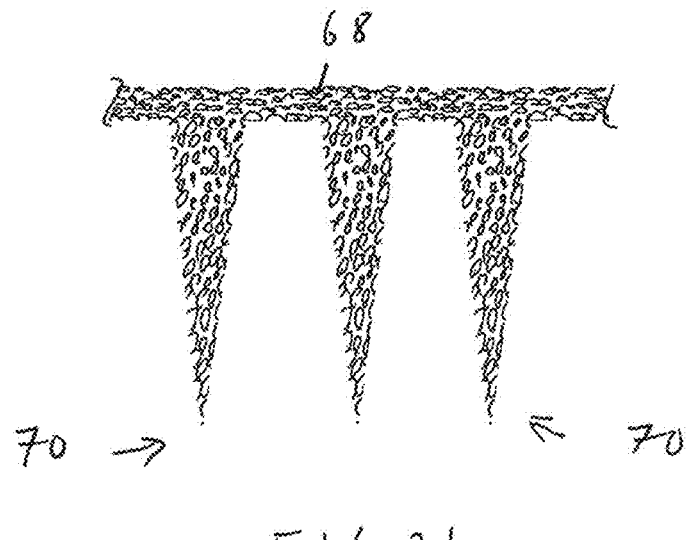
FIG. 21 illustrates an open pore material in the shape of microneedles, according to an embodiment of the present disclosure.
Figure 22:
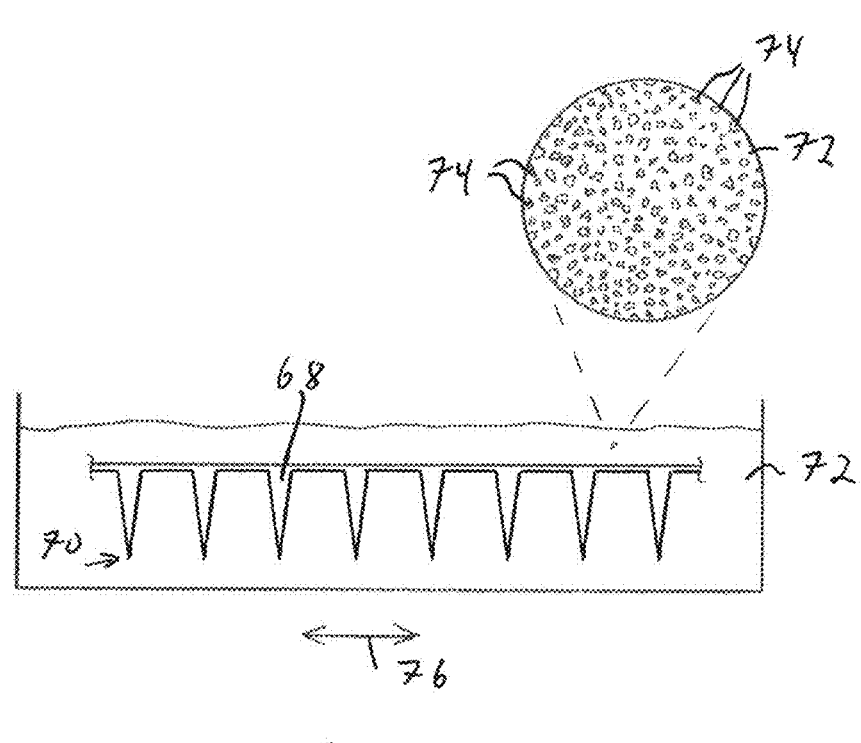
FIG. 22 is a schematic representation of immersing the open pore material of FIG. 21 in a carrier liquid including the drug in particular form, according to an embodiment of the present disclosure.
Figure 23:
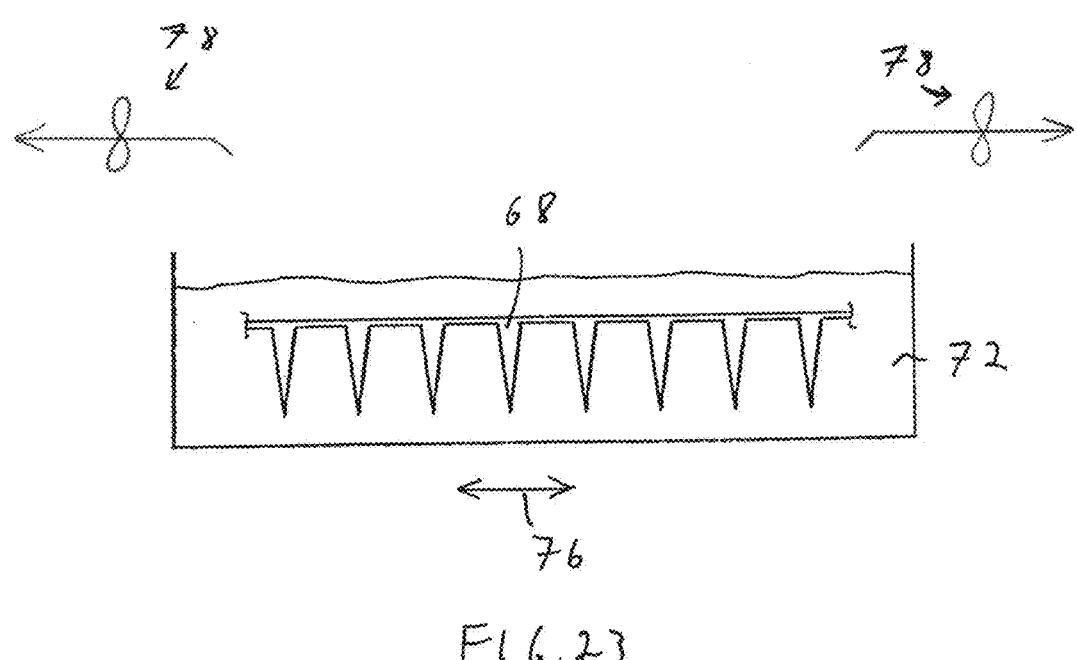
FIG. 23 is a schematic representation similar to FIG. 22 showing agitation and evaporation of the carrier liquid, according to an embodiment of the present disclosure.
Figure 24:
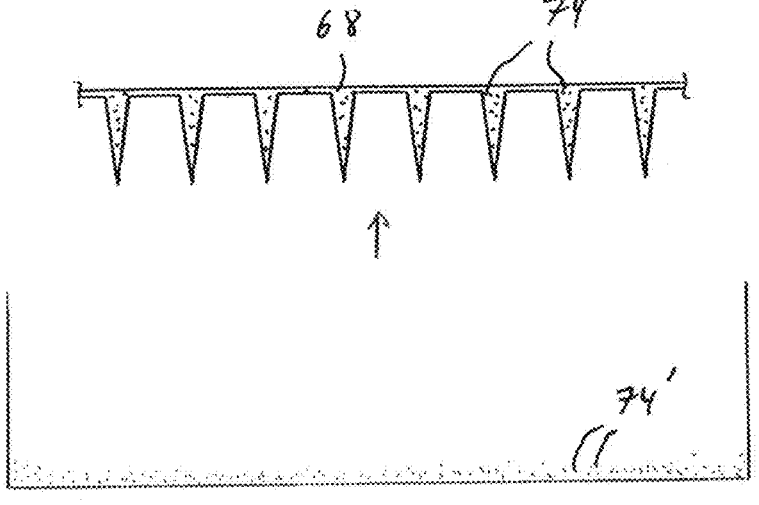
FIG. 24 illustrates the open pore material containing the drug in particulate form, according to an embodiment of the present disclosure.
Figure 25:
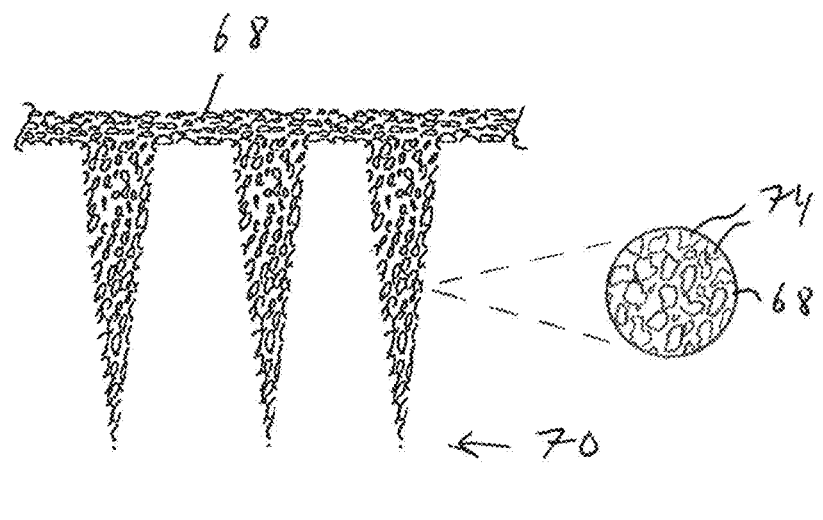
FIG. 25 illustrates the open pore material containing the drug in particulate form, according to an embodiment of the present disclosure.

FIG. 21 shows the resulting open pore material 68 that remains formed in the shape of microneedles 70. The resulting open pore material 68 is then immersed in a bath of a carrier liquid 72 that includes a high concentration of the drug 74 in particulate form (not dissolved) as shown in the enlarged view of FIG. 22. In some embodiments the drug 74 may be dissolved in the carrier liquid 72 and later return to particulate form, post evaporation of the carrier liquid. The level of immersion of the open material may also be controlled to limit the amount of the material (e.g., microneedles only) that is immersed in the carrier liquid, which limits the amount and location of the drug deposited into the open pore material, for example limiting the drug to be deposited only in the microneedles or only in the tips of the microneedles. The drug particulates may have sizes below about 100 micrometers in the largest dimension, or even below about 20 micrometers in the largest dimension. In some embodiments the drug particulates have sizes below 1 micrometer in the largest dimension. In some embodiments the drug particulates have sizes below 100 nanometers in the largest dimension. The carrier liquid 72 with the drug 74 are then agitated (as shown at 76) with respect to the open pore material 68 in order to flow the desired amount of the drug 74 in the carrier fluid 72 into the open pores. With further reference to FIG. 23, once the desired amount of the drug is flowed into the open pores, the carrier liquid is evaporated, for example, with the use of fans or blowers 78. The open pore material 68 that now contains the drug in particulate form is then removed, leaving residual drug 74 that may be collected and reused as shown in FIG. 24. FIG. 25 shows the open pore material 68 with the drug in particulate form 74 within the composite.

Figure 27:
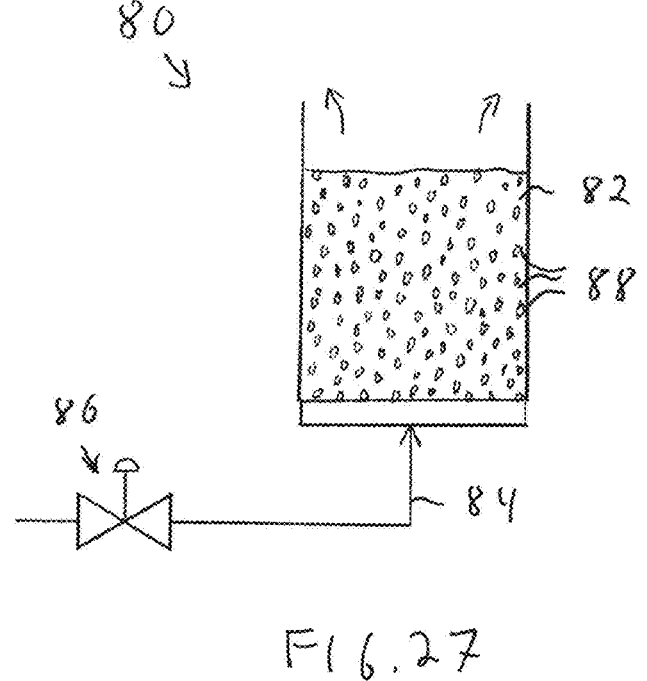
FIG. 27 is a schematic representation of the creation of the open pore material by the application of a gas through a resin, according to an embodiment of the present disclosure.

In further aspects, an open-pored material is created through infusion of gas bubbles (or a bubble-forming gas) through a resin or liquid metal prior to casting and cooling or curing. For example, FIG. 27 shows at 80 a resin or liquid metal 82 through which a gas 84 (e.g., nitrogen) is provided via a valve 86. The gas (and the viscosity of the resin or liquid metal 82) may be selected such that a substantial portion of the gas remains (e.g., in the form of bubbles) 88 in the resin or liquid metal 82, and remain in high enough concentration to result in an open pore material. The gas filled material 82 is then cast onto a mold, cooled or cured and filled with drug particulates as discussed above.

In an aspect, the present disclosure provides a method of fabricating a microneedle for transdermal drug delivery. The method can include: stretching a microneedle mold having at least one microneedle-forming cavity to expand a size of the at least one microneedle-forming cavity; casting a mixture of a drug and a biocompatible resin on the microneedle mold such that the mixture fills the expanded microneedle-forming cavity, wherein the drug is in a solid particulate form and has a particulate size of 10 nanometers to 100 micrometers; allowing the microneedle mold to contract to an original size of the microneedle mold; curing the mixture in the microneedle-forming cavity to provide the microneedle, the microneedle being solid and porous, the drug being embedded in pores of the microneedle; and removing the microneedle from the microneedle mold.

In an aspect, the present disclosure provides a method of fabricating a microneedle patch for transdermal drug delivery. The method can include: stretching a microneedle mold having a microneedle-forming cavity beyond an original size of the microneedle mold; casting a mixture of a drug and a biocompatible resin on the microneedle mold such that the mixture fills the microneedle-forming cavity, wherein the drug is in solid particulate form and has a particulate size of 10 nanometers to 100 micrometers; allowing the microneedle mold to contract to the original size of the microneedle mold; curing the mixture in the microneedle-forming cavity to provide a microneedle, the microneedle being solid and porous, the drug being embedded in pores of the microneedle; casting an elastic polymer on the microneedle mold; curing the elastic polymer to bond the elastic polymer to the microneedle and to provide the microneedle patch; and removing the microneedle patch from the mold.

The methods described herein can also include additional steps relating to fabrication of the microneedle mold. Such additional steps can include: laser cutting one or more microneedle-shaped depressions into a first material to provide a first mold; casting a second material onto the first mold to fill the one or more microneedle-shaped depressions with the second material; curing the second material to provide a second mold having one or more microneedles formed within each of the one or more microneedle-shaped depressions; removing the cured second mold from the first mold; plasma treating a surface of the cured second mold having the one or more microneedles; applying a release layer to the surface of the cured second mold; casting a third material onto the surface of the cured second mold; curing the third material to provide the microneedle mold having the microneedle-forming cavity; and removing the microneedle mold from the cured second mold. The laser-cutting can include use of a crossover line pattern. The first material can be an acrylic sheet, the second material can be a silicone elastomer, and the third material can be an ultra-elastic silicone rubber. Applying the release layer can involve silanizing the surface of the cured silicone elastomer. The silanizing can be performed with trichloro(1H, 1H, 2H, 2H-perfluorooctyl) silane.

The methods described herein can also include additional method steps relating to making the mixture of biocompatible resin and drug. Such additional steps can include: grinding the drug into fine particles having a particle size of 10 nanometers to 100 micrometers; and mixing a 1:1 ratio of the ground drug and the biocompatible resin to provide a casting paste.

The curing steps of the methods described herein can be achieved by curing methods understood to those having ordinary skill in the polymeric arts, including but not limited to, photocuring via exposure to curing radiation, such as ultraviolet light and/or light having a wavelength of 405 nm.

The mixture of the drug and the biocompatible resin, casting paste, can have a 1:1 ratio of drug to biocompatible resin. The mixture can be a paste. The mixture can be an emulsified homogeneous mixture.

Use and Performance of Microneedles

Figure 8A:
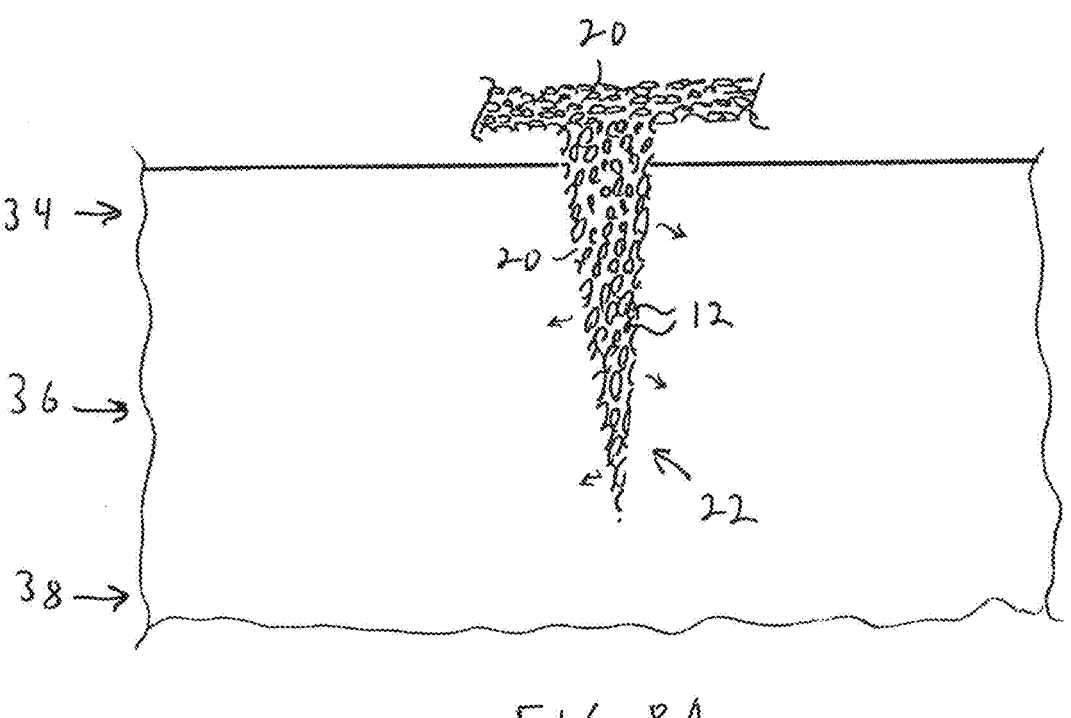
FIG. 8a illustrates a microneedle in a dermal environment, according to an embodiment of the present disclosure.
Figure 8B:
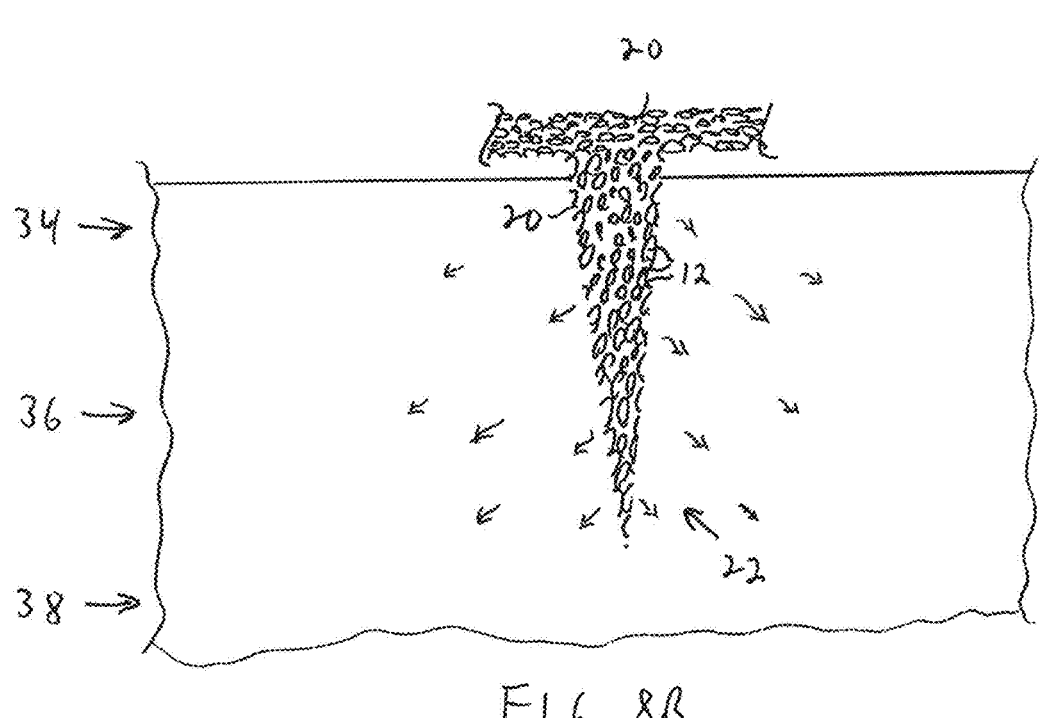
FIG. 8b illustrates diffusion of the drug from the microneedle into a dermal environment, according to an embodiment of the present disclosure.

FIGS. 8A and 8B show a microneedle 22 with the drug in particulate form 12 in the cured porous polymeric material 20, with the microneedle 22 applied to the skin and extending through the epidermis layer 34, into the dermis layer 36 and optionally into the subcutaneous layer 38. In accordance with various aspects, the drug may be in the entire cured porous polymeric material, or the drug may be provided only in the microneedles. As shown with reference to FIG. 8B, over time, more drug is diffused into the dermal environment.

The drug particulates that do not initially have direct contact with the environment external to the microneedle structure become available within the microneedle as adjacent drug particulates are dissolved by an external solvent e.g. interstitial fluid of the skin. Upon release and dissolution of the drug, the spent microneedle is a highly porous structure of empty pores (e.g., wherein the pores are occupied by water, a solvent, or a gas). In essence, a hard microneedle is provided that can easily penetrate the skin while having a clinically significant drug loading capacity. The drug may be water soluble and the porous material may be hydrophobic, or the drug may be lipid soluble and the porous material may be hydrophilic.

Figure 31:
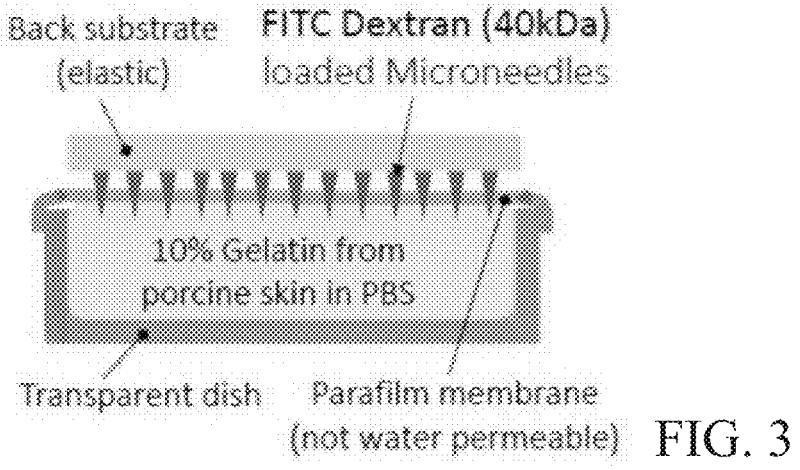
FIG. 31 illustrates a test specimen with an array of microneedles including FITC-Dextran, according to an embodiment of the present disclosure.
Figure 32:
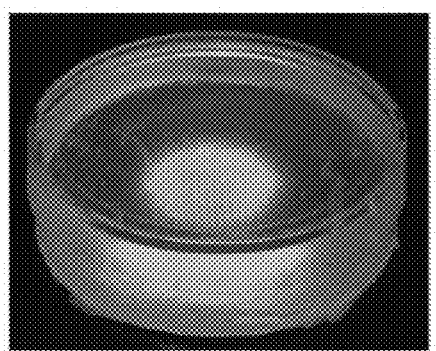
FIG. 32 illustrates a test specimen with an array of microneedles in a simulated dermal fluid, according to an embodiment of the present disclosure.

Over time (e.g., about 10 minutes, 15 minutes, 30 minutes, one hour, several hours, 7 hours, 8 hours, 10 hours, 12 hours, 24 hours, 2 days, 3 days, 5 days, 7 days, 14 days, 21 days, or 30 days), microneedles may release a drug into a dermal environment. FIG. 31 shows a test specimen with the array of microneedles (e.g., 10 by 10 or 20 by 20; 1 by 20 or 5 by 14) in a simulation dermal fluid, composed of 10% gelatin from porcine skin mixed with PBS. With reference to FIG. 32, the microneedles may include Fluorescein isothiocyanate-dextran (FITC-Dextran) and may be provided through a non-water permeable paraffin membrane to a 10% gelatin from porcine skin in the simulation. The release rate of the drug may diminish over time, yet still provide some amount of discharge even after two hours.

In some embodiments the drug-loaded microneedle array patch (FIG. 7) may be applied to the skin for less than 1 minute. In some embodiments the drug-loaded microneedle array patch may be applied to the skin for between about 1 and 5 minutes. In some embodiments the drug-loaded microneedle array patch may be applied to the skin for between about 5 and 30 minutes. In some embodiments the drug-loaded microneedle array patch may be applied to the skin for between about 30 and 60 minutes. In some embodiments the drug-loaded microneedle array patch may be applied to the skin for between about 1 and 8 hours. In some embodiments the drug-loaded microneedle array patch may be applied to the skin for between about 4 and 8 hours. In some embodiments the drug-loaded microneedle array patch may be applied to the skin for between about 8 and 12 hours. In some embodiments the drug-loaded microneedle array patch may be applied to the skin for between about 6 and 10 hours. In some embodiments the drug-loaded microneedle array patch may be applied to the skin for between about 12 and 24 hours. In some embodiments the drug-loaded microneedle array patch may be applied to the skin for between about 1 and 24 hours. In some embodiments the drug-loaded microneedle array patch may be applied at night and removed the following morning. In some embodiments the drug-loaded microneedle array patch may be applied to the skin for between about 1 and 7 days. In some embodiments the drug-loaded microneedle array patch may be applied to the skin for between about 7 and 14 days. In some embodiments the drug-loaded microneedle array patch may be applied to the skin for between about 14 and 21 days. In some embodiments the drug-loaded microneedle array patch may be applied to the skin for between about 21 and 28 days.

Due to the customizable nature of the fabrication process previously described herein (and additionally described in (WO 2019/203888), the geometry of the array consisting of at least one microneedle can take many shapes and sizes. This is significant for use cases, as the microneedle array patch can be designed to conform to specific locations on a patient's body, depending on the indication and desired location for delivery. In some embodiments the array can be a thin long strip (e.g. 1 by 100 or 2 by 200 microneedles) to deliver a drug along a patient's limb, for example. In some embodiments the array can be arranged in a circle with a central region void of any microneedles to deliver a drug around a patient's joint, for example. In some embodiments, the microneedle array can be in the form of a recognizable shape e.g. a smiley face or company logo to meet the needs of commercial marketing.

When the microneedles are introduced to a solvent-rich environment, the drug portion dissolves and diffuses into the surrounding environment. This dissolution/diffusion process continues to the point that all or substantially all of the drug in the interconnected pores within the porous material releases into the surrounding environment. Now, for this to work, the drug and the resin should be immiscible. The choice of resin to produce the porous material may be one that is hydrophobic in nature and therefore would work most efficiently with water-soluble drugs such as peptides, proteins, and monoclonal antibodies. The rate of drug release has been shown to be readily tunable by controlling the particle size of the drug dried powder. The drug particle size is accurately controllable using, for example, a vibration based-mini mill, or a spray drying method.

Figure 13:
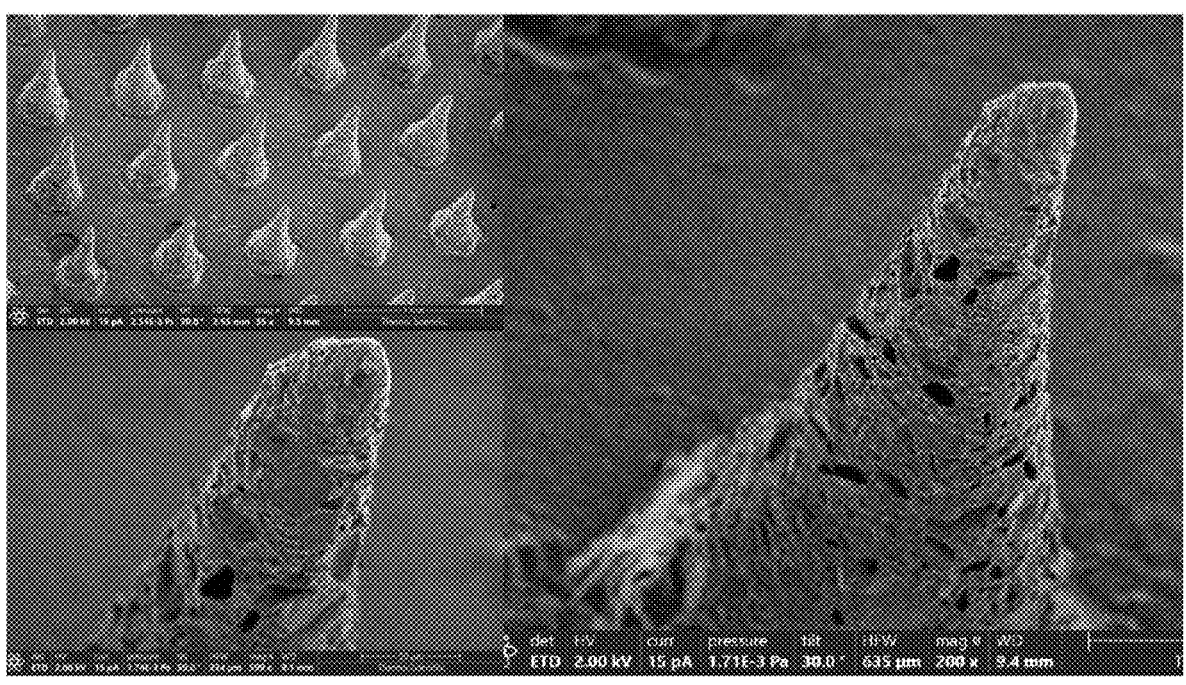
FIG. 13 shows scanning electron micrographs of microneedles, according to the present disclosure.
Figure 14:
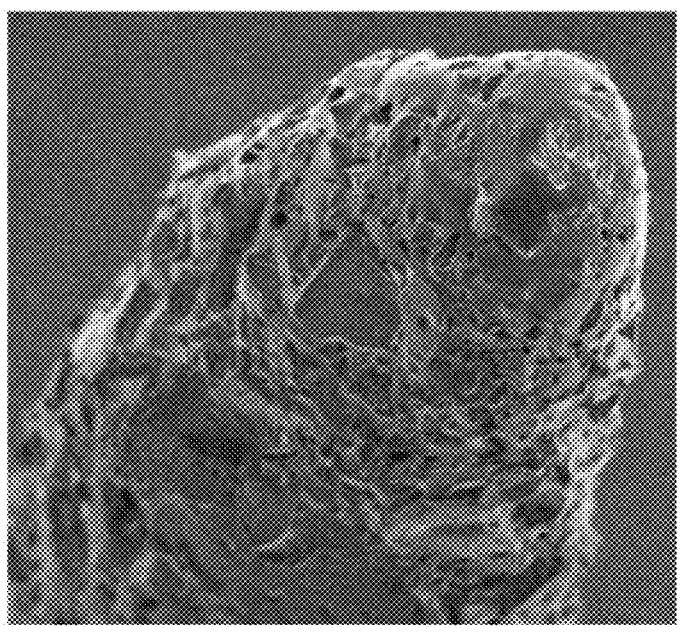
FIG. 14 shows a scanning electron micrograph of a microneedle after release of the drug, according to the present disclosure.

FIG. 13 shows (in the upper left) a scanning electron micrograph of a portion of a microneedle of an aspect of the present invention after release of the drug. An enlarged portion of a microneedle after release of the drug is shown in the right side, and a further enlarged view of the microneedle is shown in the lower left side of FIG. 13. Certain (larger) areas may be seen as being empty (dark) following dissolution and release of the drug. FIG. 14 shows a further enlarged view of a tip of the microneedle following release of the drug.

Figure 28A:
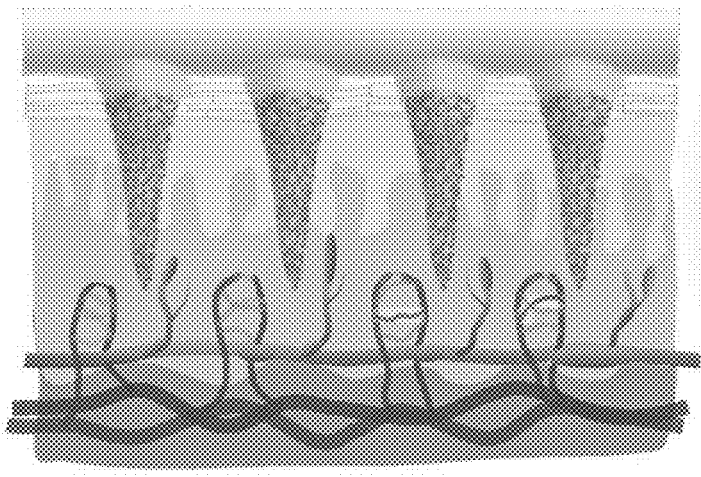
FIGS. 28*a*-28*c* illustrate views at different times as the microneedles enter a dermal environment and the drug is released, according to an embodiment of the present disclosure.
Figure 28B:
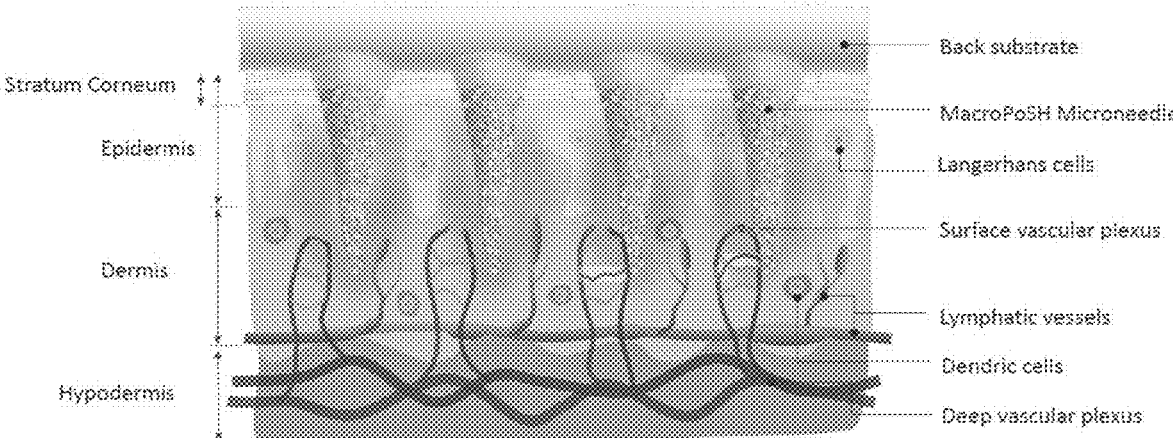
Figure 28C:
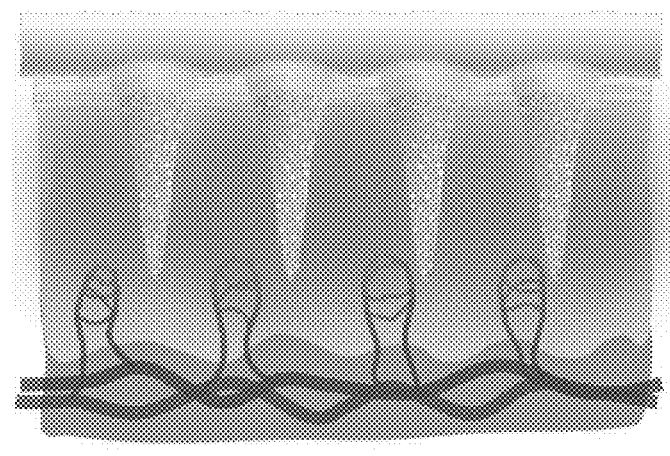

FIGS. 28A-28C show views at different times as the microneedles (e.g., any of the microneedles discussed above) enter a dermal environment and the drug is released from the open pore material. In particular, the microneedles may penetrate the stratum corneum and epidermis, entering the dermis to provide release of the drug to the epidermis, dermis and hypodermis regions, permitting delivery of the drug to the Langerhans cells, surface vascular plexus, lymphatic vessels, dendritic cells and deep vascular plexus.

The previously described fabrication process can be used to optimize the microneedle patch mechanics including the back substrate mechanical and geometrical properties, and microneedle shape to achieve maximum penetration efficiency. In some embodiments the microneedles are securely assembled on a thin transparent elastic back-substrate by using an elastic resin compatible with the polymer forming the microneedles. In some embodiments the back substrate further attaches to a layer of adhesive. In some embodiments the combination of the back substrate and the thin adhesive are about 100 micrometers in thickness. As a result of having a thin, flexible adhesive patch, the patch firmly adheres to the skin surface and is very conformal. The thin substrate also significantly helps with microneedle penetration compared to a thick substrate (thickness greater than about 1 millimeter). This way, force directly transfers to the microneedles (rather than diffusing into back substrate), and individual microneedles can be subjected to force to achieve effective penetration.

By leveraging the use of a thin, flexible back substrate, the microneedle arrays described herein, comprised of macroPoSH microneedles can avoid the "bed of nails" principle, where distributing force across multiple points over a given area at the same time can lead to very poor dermal penetration, despite using sharp objects. By using a thin, flexible patch, the local force can apply to individual microneedles at a time in order to avoid the bed of nails resistance and ensure consistent, effective penetration into the skin.

Figures 15, 16:
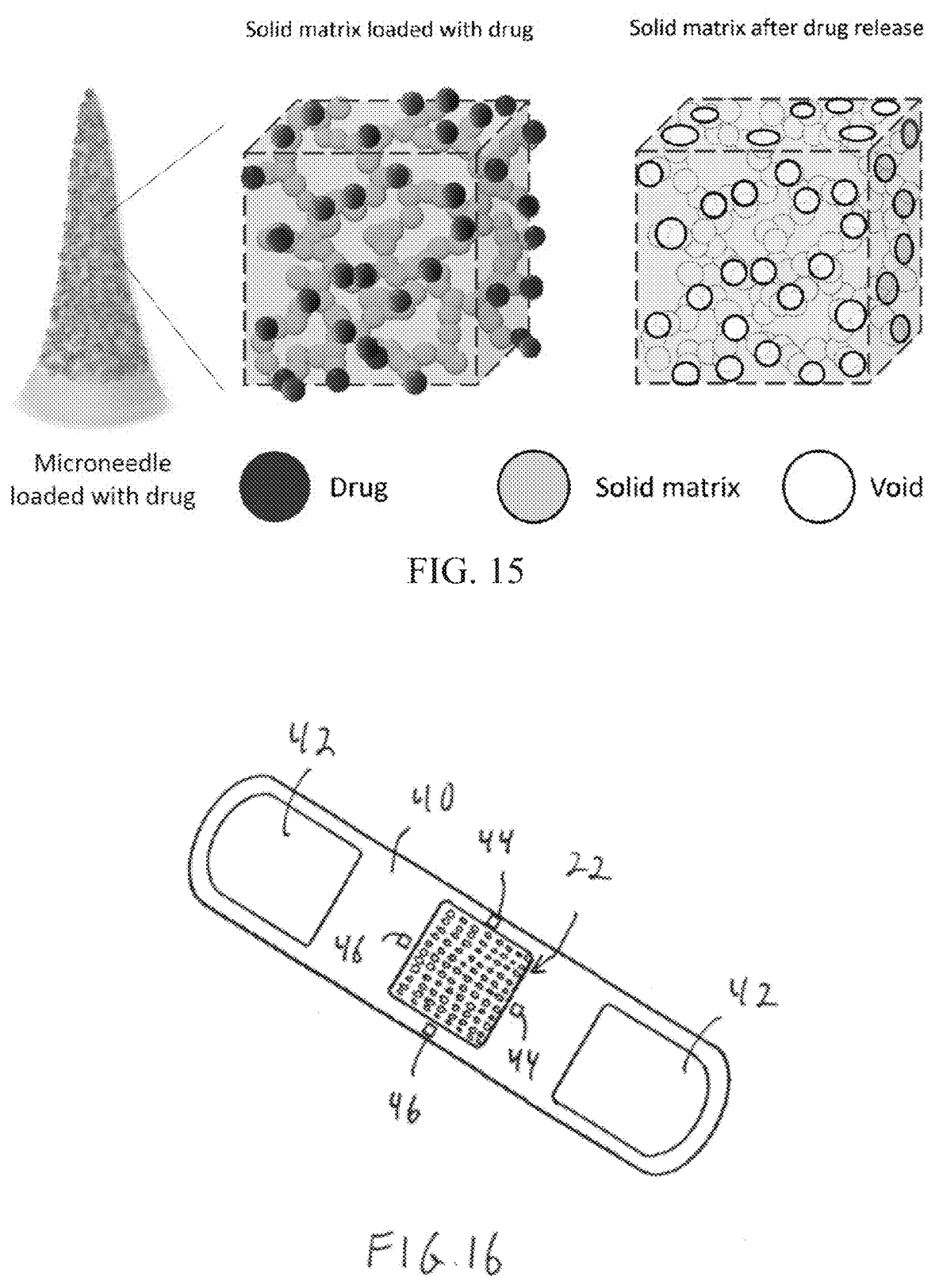

FIG. 15 shows diagrammatically a solid matrix, e.g., a polymer, loaded with a drug and the solid matrix after release of the drug. With reference to FIG. 16, a bandage 40 with adhesive 42 in accordance with a further aspect of the present invention may include one or more light emitters 44 as well as one or more light sensors 46. The light sensors 46 may even be visible through the bandage to permit a user to know when the drug has been fully discharged from the bandage.

FIG. 26A shows that a set of microneedles on a thick back-substrate may provide uneven penetration into a subject at an area that is not flat. This problem can be solved as shown in FIG. 26B, a set of microneedles on a thin (flexible) back-substrate may be applied to conform to an area that is not flat and provide a much more uniform microneedle penetration into the subject.

Other Uses

The microneedles and microneedle patches described herein can be useful for application to, and drug delivery across, anatomic structures and membranes other than skin, e.g., mucosa (oral, buccal, sublingual, nasal), gingiva, conjunctiva, sclera, retina, ear canal, tympanic membrane, epithelium (e.g., gastrointestinal, respiratory, vaginal, uterine, vesicular, urethral), serosa, and arterial or venous intima.

Microneedles disclosed herein can also find use in veterinary medicine, e.g., pets and livestock, and particularly in mammals.

Monitorable Systems

Additionally, the system may permit tracking of the release of the drug from the microneedle as the optical properties of the needles change once the drug diffuses from the microneedles (note that for high drug to resin ratios—even for 1:1 ratios—the microneedles are optically translucent after fabrication, but once the drug is out of the microneedle, due to significant increase in porosity of the structure, the microneedles look optically opaque (depending on the resin used to make them they may look whitish or yellowish or so on). This significant change in optical property can be readily used to track an amount of drug released into skin from the patch over time, and therefore digitally track the dose received by the patient in real-time. A photosensor and optional light source may be provided to monitor the discharge of the drug, either by measuring light transmittance or reflection of one or more microneedles.

As described hereinabove, a microneedle can include a marker that is released with the drug into the patient. Samples from the patient, e.g., blood or urine samples, can be tested for the marker. Skin, including the application site, can be examined for the marker. Other structures, such as the eyes or superficial blood vessels can be examined for the marker.

EXAMPLES

Microneedle Fabrication Procedure

A cross-over-lines (COL) fabrication procedure was used to make microneedle patches, as shown in FIG. 34a. A CO$_2$ laser (Boss LS-1416 from Boss Laser, LLC; Sanford, FL, USA) was used to create negative volume on Clear Scratch- and UV-Resistant Cast Acrylic Sheets (part number 8560K359. McMaster-Carr; Princeton, NJ, USA). The engraved acrylic mold was washed with isopropanol and distilled water to remove any dust or other foreign matter from the surface and engraved areas. A nitrogen gun was used to remove the excess water on the surface. The mold was then dried in an atmospheric oven at 80° C. for 30 minutes. Then, polydimethylsiloxane (PDMS, Dow Sylgard™ 184 Silicone Elastomer; Dow Silicones Corporation in Midland, MI, USA) was cast on the acrylic sheet. The PDMS-casted sheet was degassed and subsequently cured in the oven at 80° C. for 2 hours. After complete curing of the PDMS, the PDMS microneedles were peeled off of the acrylic sheet and were treated with oxygen plasma to activate the surface of the PDMS microneedles. The PDMS microneedles were then silanized with trichloro(1H, 1H, 2H, 2H-perfluorooctyl)silane (SKU: 448931-10G, from MilliporeSigma; Burlington, MA, USA) under vacuum in a desiccator overnight. Ecoflex™ 00-50 (Smooth-On, Incorporated, Macungie, PA, USA) with the ratio of 1:1 was cast on the silanized PDMS microneedles followed by curing at room temperature. The silane layer creates a barrier between the PDMS microneedles and the Ecoflex mold and prevents them from bonding together, facilitating their detachment.

The achieved Ecoflex mold is extremely flexible and stretchable, and can be stretched to about three times its original size. Having a stretchable mold allows the microneedle patches to be made in a much shorter time. The final Ecoflex mold can be used to create microneedles made from different polymers. The drug solution or powder can be cast on the stretched mold. Here, we introduce a new paste comprised of biocompatible resin and the drug (see "Drug-Loaded Microneedles" section). The Ecoflex mold was stretched, and the resin/drug paste was cast on the stretched Ecoflex mold. Then, the mold was put under rest mode and the excessive drug paste was removed from the surface of the mold. The paste embedded in the Ecoflex mold was then photo-cured by exposure to 405 nm light. After curing the paste, a thin layer of elastic polymer was cast on the surface of the mold as a back substrate and cured under UV light to harden the back substrate. Finally, the microneedles with the substrate were peeled off of the mold with the needles bonded to the back substrate. Referring to FIG. 34b, a 6 centimeter by 20 centimeter microneedle patch having conformability and flexibility was prepared. Microneedle patches may be fabricated in any form and shape according to this procedure. The method provides a high drug loading capacity, and the drugs can be distributed without the need for cold refrigeration.

Dye-Loaded Microneedle Patch for In Vitro Release

In order to show in vitro release of the microneedles visually, a resin/dye paste was prepared. A biocompatible resin (Dental SG) from Formlabs (Somerville, MA, USA) and sulforhodamine B (SKU: 230162-5G, MilliporeSigma; Burlington, MA, USA) as dye were used. Due to the small size of the microneedles, the dye particles were ground into finer particles with smaller sizes. The encapsulation of unground and ground dye in microneedles was compared by preparing microneedles with both unground and ground sulforhodamine B particles. The unground and ground particles of the dye are shown in FIGS. 35a and 35b, respectively, and the size distribution of the unground and ground dye is shown in FIG. 35c. On average, the unground and ground dye particles had particle sizes of about 50 micrometers and 6 micrometers, respectively. As shown in FIG. 35d, the unground dye particles exhibited poor encapsulation into the microneedles due to the larger particles of the dye. On the other hand, improved dye encapsulation was observed with the smaller ground dye particles (see FIGS. 35e and 35f). FIG. 35f shows dye-loaded microneedles with a star-shaped base structure for more robustness and rigidity. FIG. 35g shows schematic representations of a microneedle patch prepared for in vitro dye release experiments. A solid acrylic ring was added around the substrate so that the microneedle patch could be held and applied easily (see FIG. 35g). The in vitro dye release experiment is shown schematically in FIG. 35h. A 10% gelatin (gelatin from porcine skin, SKU: G2500-1KG from Millipore Sigma) solution was prepared as a model tissue and was poured in a petri dish. Then, it was placed in the refrigerator for 20 minutes to further solidify. A thin layer of parafilm (Parafilm ° M, Amcor; Zurich, Switzerland) was then used as a skin model to cover the gelatin solution in the petri dish. The top and bottom side of the prepared dye-loaded microneedle patch is shown in FIGS. 35i and 35j. After inserting the microneedle patch into the parafilm-covered gelatin, visible release of the dye into the gelatin solution occurred (see FIG. 35l). FIG. 35k shows the release of the dye after 10 minutes.

Drug-Loaded Microneedles

Lidocaine and ibuprofen are drugs used for pain relief. These drugs were chosen for preparing pain relief patches.

First, the in vitro release profile of lidocaine and ibuprofen was investigated to verify their diffusion mechanisms. Next, experiments were conducted to determine if the mixture of cured resin and drug (lidocaine or ibuprofen) retains the characteristics of lidocaine and ibuprofen and does not change their respective properties. FTIR spectroscopy measurements were conducted on the cured resin/drug to investigate whether lidocaine and ibuprofen retain their respective properties. In addition, the mechanical properties of drug-loaded microneedles were investigated.

In Vitro Drug Release of Lidocaine and Ibuprofen Microneedles

For the in vitro drug release experiments, ibuprofen sodium salt (SKU: 11892) and lidocaine hydrochloride monohydrate (SKU: L5647) purchased from MilliporeSigma (Burlington, MA, USA) were used. Ibuprofen and lidocaine concentrations were detected by UV-Vis spectroscopy at 222 nanometers nm and 263 nm, respectively. Different concentrations of ibuprofen and lidocaine were prepared by dissolving them in Dulbecco's phosphate buffered saline (DPBS) (MilliporeSigma (SKU: 59331C)). The absorbance peaks at 222 nm and 263 nm for ibuprofen and lidocaine, respectively, were detected using an Evolution 220 UV-Vis spectrophotometer from Thermo Fisher Scientific, Inc. (Waltham, MA, USA). The ibuprofen and lidocaine solutions were swept at 190-300 nm and 254-300 nm wavelengths, respectively, for various concentrations, as shown in FIGS. 36a and 36b. Calibration curves for ibuprofen and lidocaine are shown in FIG. 36c. The ibuprofen sodium salt and lidocaine hydrochloride monohydrate were ground by a Chulux grinder (with four blades) for three minutes to make finer particles. Then, ibuprofen and lidocaine fine particles were mixed with biocompatible resin at a 1:1 ratio. The microneedle patch was then fabricated by the method explained in the "Microneedle Mold Fabrication Procedure" section. Each microneedle patch had 100 microneedles. Multiple petri dishes (one petri dish for each timestamp) containing DPBS were placed inside an incubator at a temperature of 37° C. At each timestamp, the patch was transferred to a fresh DPBS-containing petri dish. As shown in FIG. 36d, the release profile shows that each patch (containing 100 microneedles) releases approximately 1 milligram of drug in DPBS solution.

In Vitro Drug Release of a Large Molecule and Modulation of the Release Profile Based on Particle Size FIG. 31 shows the microneedles including FITC-Dextran (49 kDa) that may, for example, be provided through a non-water permeable paraffin membrane to a 10% gelatin from porcine skin in a simulation. FIG. 32 shows a test specimen with an array of microneedles (e.g., 10 by 10) in a simulated dermal fluid. FIG. 33 shows cumulative FITC-Dextran release of two different formulated needle patches. By reducing the particulate size (to a limit), the rate of drug release and the total amount of drug release may be increased or adjusted. Modulating the rate and profile of the drug release can be important to stay within the therapeutic window for a longer period of time and achieve better clinical outcomes for a given drug.

Interaction Between Polymers and Drug: FTIR Spectroscopy

FTIR spectroscopy was used to evaluate possible changes in the encapsulated drugs during the fabrication process. A Nicolet 6700 (ThermoScientific™; Waltham, MA, USA) with a Smart™ iTX ATR accessory having a diamond crystal was used. Fourier transform infrared attenuated total reflectance (FTIR-ATR) spectra showed the presence of the following characteristic peaks in lidocaine: N—H stretching at 3450 and 3385 cm$^{-1}$, amide C=O stretching at 1655 cm'. An obvious increase in the intensity of the peak at 1655 cm$^{-1}$ related to the amide C=O stretch was observed (see FIG. 36e). In FTIR, an increase in the peak intensity usually reflects an increase in the amount (per unit volume) of the functional group associated with the molecular bond, whereas a shift in peak position usually reflects a change in the hybridization state or electron distribution in the molecular bond. Thus, the decrease in the intensity of amide C=O in lidocaine/resin samples was attributed to the reduction in the lidocaine ratio in the samples. The FTIR was checked with a manufacturer data sheet for lidocaine hydrochloride monohydrate and there were peaks at 3450, 3400 and 3200 cm$^{-1}$ as it is seen with our data in FIG. 36e. Furthermore, no shifts in peak positions were seen in FTIR spectra of ibuprofen/resin (see FIG. 36f). The peaks at 1721 cm$^{-1}$ and 3400 cm$^{-1}$ are assigned to the stretching vibrations of C=O and O—H, respectively. These FTIR observations confirmed that the chemical structure of lidocaine and ibuprofen remained unchanged during the fabrication process.

Histology Test, Surface Morphology, and Mechanical Behavior

A histology test was performed to confirm the insertion of the microneedles into the skin. A four-month-old male Yorkshire pig skin was used for the histology test. The skin was shaved and cut using a 10 #scalpel blade and was placed into a specimen container filled with sterile 0.9% saline. The microneedle patch was inserted on the skin using a thumb pressure. The microneedle patch was peeled off shortly after application. The micrographs of FIG. 37a are from the H & E (Hematoxylin and Eosin) stained tissue section fixed in 10% neutral formalin. Histological examination showed that the microneedles penetrated about 600 micrometers into the skin, as shown in FIG. 37a. As shown in other similar studies, the depth of the microneedle's penetration into skin was shorter than the length of the entire microneedle due to the deformation of highly elastic skin. The mixture of resin and drug creates pores and cavities, as shown in FIG. 37b. The drug is released after administering the microneedles, leaving empty cavities behind. The porous microneedles of the present disclosure exhibit high robustness due to the high tensile strength of the resin (73 Megapascals (MPs)). The mechanical behavior of an individual resin/drug microneedle is shown in FIG. 37c. The compression test was performed with Instron (Norwood, MA, USA). These microneedle tips started to break down at a force of 0.26 N per needle. According to previous experiments, this provides a four-fold margin of safety over the force (0.058 N per needle) needed for insertion into skin using microneedles of this geometry. The resin/drug microneedles of the present disclosure were compared to polyethylene glycol diacrylate (PEGDA) based microneedles. The PEGDA microneedles showed strong mechanical properties for easy skin penetration in previous studies. Here, we confirm the higher robustness of resin/drug microneedles of the present disclosure compared to PEGDA based microneedles (see FIG. 37d). The PEGDA microneedles were prepared using a drug solution of 500 milligrams per milliliter (mg/ml) and PEGDA (Millipore Sigma, SKU: 437441-500ML) with molecular weight of 575 mixed with 1% photo-initiator (2-hydroxy-4'-(2-hydroxyethoxy)-2-methylpropiophenone (Millipore Sigma, SKU: 410896-10G)). The drug solution and PEGDA solution were mixed in a 4:1 (v/v) ratio. The prepared solution was added to the microneedle mold and cross-linked by UV-light irradiation at a wavelength of 365 nm.

In Vitro Bioassay to Assess Efficacy of a Monoclonal Antibody after Microneedle Patch Fabrication To evaluate the effectiveness of the treatment being delivered through microneedles an in vitro model, a whole blood assay was performed using Rituximab (RTX) as the drug. Rituximab is a chimeric monoclonal antibody against the protein CD20, which is primarily found on the surface of immune system B cells. When it binds to this protein it triggers cell death via Complement-Dependent Cytotoxicity (CDC). RTX is a good model to evaluate the mAb delivery mechanism mainly because of its clear pharmacodynamics outcome, the depletion of CD20+B-Cell in whole blood. Microneedle patches with five different amounts of RTX and a constant polymer-to-drug ratio were incubated in freshly collected human blood in a 24-well plate. Flow cytometry was used to quantify CD20+ and CD19+ cells in each well. FIG. 29 shows CD20+ fluorescence for six samples. CD20+ cells are present in samples (a) through (c) on the left but absent from samples (d) through (f) on the right. The conditions are as follows: (a) Buffy coat and serum without microneedle (MN) exposure and prior to incubation; (b) Blood without MN exposure and after 4 h incubation; (c) Blood with exposure to an inert MN after incubation; (d) Blood after incubation with one MN (20 μg RTX); (e) blood after incubation with five MNs (100 μg RTX); and (f) blood after incubation with 200 MNs (4 mg RTX). Thus, CD20+ cells were present in blood samples (a) through (c) not treated with RTX-loaded MN; conversely, CD20+ cells were depleted from blood samples (d) through (f) treated with 1, 5 or 200 MN. Compared to the control, the RTX-loaded microneedle patches showed dramatic decreases in CD20+ and CD19+ counts.

The results show that (1) in vitro analysis with fresh blood can be used to assess the pharmacodynamics of different forms of microneedle patches; (2) RTX-loaded microneedle patches cause the expected PD effect of B cell depletion; and (3) the activity of RTX is preserved after completion of the microneedle patch manufacturing process.

In Vivo Delivery of Rituximab to Non-Human Primates

An in vivo primate study was performed to compare the systemic pharmacodynamic effect of rituximab (RTX) following intravenous (IV) delivery versus microneedle-mediated, transdermal (TD) delivery in African green monkeys. FIG. 30 at (a) shows two applied patches, as well as the area following removal of the patches in transdermal delivery involving monoclonal antibodies. The pharmacodynamic effect was quantified by the measurement of circulating B cells by flow cytometry (all these graphs are generated by flow cytometry), employing rituximab as a tool compound to assess the ability of a novel microneedle formulation and delivery technology to achieve systemic bioavailability of macromolecules (e.g. monoclonal antibodies) following transdermal delivery. Rituximab administration both IV and TD resulted in B-cell depletion. The most significant B-cell depletion in blood was observed following IV dosing in the first week, however, daily administration of 2 patches of RTX loaded microneedle has shown significant depletion as well (reaching 81%). This is shown in FIG. 30 at (c). FIG. 30 at (b) shows the flow cytometry data from animals that received the daily administration of 2 patches, showing significant B cell depletion from baseline to Day 7 (lower right quadrant). The depletion over time for the two patches is shown in FIG. 29 for 0, 1, 7, 14 and 21 days.

The invention claimed is:

1. A microneedle for delivering a drug, the microneedle comprising:

a solid material comprising:
a solidified form obtained from a flowable material; the flowable material comprising a resin and the drug in particulate form;
the solidified form comprising a resin matrix comprising a plurality of pores in the resin matrix formed by spatial exclusion imposed by the presence of the drug in particulate form, wherein the plurality of pores are interconnected and distributed throughout the solidified form, the drug in particulate form being contained within the plurality of pores; and
a sharp apex; wherein
the particulate form is a powder, the powder comprising particles having sizes below 100 micrometers in a largest dimension.

2. The microneedle of claim 1, wherein the drug is substantially solvent-free.

3. The microneedle of claim 1, wherein the drug is substantially water-free.

4. The microneedle of claim 1, wherein more than 90% of the pores are occupied by at least one drug particulate.

5. The microneedle of claim 1, wherein more than 95% of the pores are occupied by at least one drug particulate.

6. The microneedle of claim 1, wherein more than 99% of the pores are occupied by at least one drug particulate.

7. The microneedle of claim 1, wherein more than 99.9% of the pores are occupied by at least one drug particulate.

8. The microneedle of claim 1, wherein more than 90% of volume of the pores is occupied by the drug.

9. The microneedle of claim 1, wherein more than 95% of volume of the pores is occupied by the drug.

10. The microneedle of claim 1, wherein more than 99% of volume of the pores is occupied by the drug.

11. The microneedle of claim 1, wherein more than 99.9% of volume of the pores is occupied by the drug.

12. The microneedle of claim 1, wherein the resin comprises a curable polymeric material.

13. The microneedle of claim 1, wherein the microneedle has an axial length between about 0.5 mm and about 1.5 mm.

14. The microneedle of claim 1, wherein the solid material has a hardness between 40 Shore A to 90 Shore D.

15. A device for delivering a drug, the device comprising two or more microneedles according to claim 1.

16. The microneedle of claim 2, wherein more than 90% of the pores are occupied by at least one drug particulate.

17. The microneedle of claim 3, wherein more than 90% of the pores are occupied by at least one drug particulate.

18. The microneedle of claim 2, wherein more than 90% of volume of the pores is occupied by the drug.

19. The microneedle of claim 3, wherein more than 90% of volume of the pores is occupied by the drug.

20. The microneedle of claim 1, wherein the microneedle has a drug loading of at least 10 μg/35 nL.

21. A microneedle drug delivery system for drug delivery via diffusion mediated by interstitial fluid, said microneedle drug delivery system comprising a solid material comprising:
a solidified form obtained from a flowable material, the flowable material comprising a resin and a drug in particulate form; and
the solidified form comprising a resin matrix comprising a plurality of pores in the resin matrix formed by spatial exclusion imposed by the presence of the drug in particulate form, wherein the plurality of pores are interconnected and distributed throughout the solidified form, the drug in particulate form being contained within the plurality of pores;

wherein the particulate form is a powder, the powder comprising particles having sizes below 100 micrometers in a largest dimension.

22. A method of providing time-controlled delivery of a drug, said method comprising:

providing a solid material comprising a solidified form obtained from a flowable material, the flowable material comprising a resin and a drug in particulate form, the solid material comprising a resin matrix and a plurality of pores in the resin matrix formed by spatial exclusion imposed by the presence of the drug in particulate form, wherein the plurality of pores are interconnected and distributed throughout the solidified form; the drug being contained within the plurality of pores; and permitting the solid material to come into contact with a dermal environment that comprises interstitial fluid, such that interstitial fluid contacts the drug in particulate form, causing the drug to dissolve into the interstitial fluid;

wherein the particulate form is a powder, the powder comprising particles having sizes below 100 micrometers in a largest dimension.

23. A microneedle patch for transdermal drug delivery, comprising:

a solid microneedle formed from a flowable material comprising a biocompatible resin and a drug in particulate form, the solid microneedle comprising a resin matrix and a plurality of pores in the resin matrix formed by spatial exclusion imposed by the presence of the drug in particulate form, wherein the plurality of pores are interconnected and distributed throughout the microneedle, the drug being embedded in the pores of the microneedle, the microneedle having a mechanical strength sufficient to penetrate the epidermis of skin without breaking; and a conformable back substrate bonded to the microneedle;

wherein the particulate form is a powder, the powder comprising particles having sizes below about 100 micrometers in a largest dimension.

24. A method of manufacturing a microneedle for providing time-controlled delivery of a drug, said method comprising:

providing a flowable material comprising a resin and the drug in particulate form;

curing the flowable material into a solid material comprising a solidified form obtained from the flowable material, the solidified form comprising a resin matrix and a plurality of pores in the resin matrix formed by spatial exclusion imposed by the presence of the drug in particulate form, wherein the plurality of pores are interconnected and distributed throughout the solid material;

the drug in particulate form being contained with the plurality of pores, wherein the powder comprising particles having sizes below 100 micrometers in a largest dimension.

* * * * *